(12) United States Patent
Semler et al.

(10) Patent No.: US 9,775,719 B2
(45) Date of Patent: Oct. 3, 2017

(54) EXPANDABLE VERTEBRAL BODY REPLACEMENT DEVICE AND METHOD

(71) Applicant: MUSC Foundation for Research Development, Charleston, SC (US)

(72) Inventors: Mark Evald Semler, Mount Pleasant, SC (US); Bruce Frankel, Mount Pleasant, SC (US); Joseph Ruscito, Southport, CT (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 148 days.

(21) Appl. No.: 14/665,833

(22) Filed: Mar. 23, 2015

(65) Prior Publication Data

US 2016/0278933 A1    Sep. 29, 2016

(51) Int. Cl.
*A61F 2/44*     (2006.01)
*A61F 2/46*     (2006.01)
*A61F 2/30*     (2006.01)

(52) U.S. Cl.
CPC ............... *A61F 2/442* (2013.01); *A61F 2/44* (2013.01); *A61F 2/446* (2013.01); *A61F 2/4455* (2013.01); *A61F 2/4465* (2013.01); *A61F 2/4611* (2013.01); *A61F 2002/30398* (2013.01); *A61F 2002/30405* (2013.01); *A61F 2002/30515* (2013.01); *A61F 2002/30517* (2013.01); *A61F 2002/30556* (2013.01);
(Continued)

(58) Field of Classification Search
CPC ............ A61B 17/7065; A61B 17/7068; A61B 17/7062; A61B 17/8875; A61B 17/7064; A61B 17/7082; A61B 17/8872; A61B 2017/681; A61B 17/70

USPC ................. 606/246–249, 99, 104; 623/17.11
See application file for complete search history.

(56) References Cited

U.S. PATENT DOCUMENTS 4,657,550 A     4/1987  Daher
5,083,621 A  *  1/1992  Sheridan ............ A61B 17/7001
                                                    173/164
(Continued)

FOREIGN PATENT DOCUMENTS

WO     2013173682     11/2013

OTHER PUBLICATIONS

Invitation to Pay Additional Fees from the International Searching Authority for International Application No. PCT/US2016/020209 (dated May 17, 2016).

(Continued)

*Primary Examiner* — Eduardo C Robert
*Assistant Examiner* — Tara R Carter
(74) *Attorney, Agent, or Firm* — Heslin Rothenberg Farley & Mesiti P.C.; Jacquelyn A. Graff

(57) ABSTRACT

An expandable vertebral body device, system, instrument, and methods of assembly and using the device, system, and instrument are disclosed. The vertebral body device includes a body with a first end and a second end, a first rotating member rotatably coupled to the first end, a second rotating member rotatably coupled to the second end, a first extension member moveably coupled to the first end, and a second extension member moveably coupled to the second end. The expandable cage system comprises a vertebral body device and an insertion instrument. Methods for assembling and using the vertebral body device and instrument are also disclosed.

13 Claims, 41 Drawing Sheets

(52) U.S. Cl.
CPC ............... *A61F 2002/30601* (2013.01); *A61F 2002/30774* (2013.01); *A61F 2002/30784* (2013.01); *A61F 2002/30818* (2013.01); *A61F 2002/30825* (2013.01); *A61F 2002/30836* (2013.01); *A61F 2002/4627* (2013.01); *A61F 2250/0007* (2013.01)

(56) References Cited

U.S. PATENT DOCUMENTS

| | | |
|---|---|---|
| 5,702,455 A * | 12/1997 | Saggar .................... A61F 2/44 623/17.15 |
| 6,802,867 B2 | 10/2004 | Manasas et al. |
| 7,384,431 B2 | 6/2008 | Berry |
| 7,575,601 B2 | 8/2009 | Dickson |
| 7,641,693 B2 | 1/2010 | Gutlin et al. |
| 8,157,864 B2 | 4/2012 | Rogeau et al. |
| 8,182,535 B2 | 5/2012 | Kraus |
| 8,246,680 B2 | 8/2012 | Betz et al. |
| 8,252,054 B2 | 8/2012 | Greenhalgh et al. |
| 8,366,779 B2 | 2/2013 | Dickson et al. |
| 8,540,770 B2 | 9/2013 | Woodburn, Sr. et al. |
| 8,568,482 B2 | 10/2013 | Kraus et al. |
| 8,585,763 B2 | 11/2013 | Olevsky et al. |
| 8,690,886 B2 | 4/2014 | Fedorov et al. |
| 8,721,723 B2 | 5/2014 | Hansell et al. |
| 8,740,980 B2 | 6/2014 | Merves |
| 8,992,617 B2 | 3/2015 | Woodburn et al. |
| 9,241,808 B2 | 1/2016 | Sabatino |
| 9,320,612 B2 | 4/2016 | Sournac et al. |
| 2009/0112325 A1 | 4/2009 | Refai et al. |
| 2010/0094424 A1 | 4/2010 | Woodburn et al. |
| 2010/0274357 A1 | 10/2010 | Miller et al. |
| 2013/0310938 A1 | 11/2013 | Sournac et al. |
| 2013/0331943 A1 | 12/2013 | Arnold et al. |
| 2014/0058517 A1 | 2/2014 | Sabatino |
| 2014/0088708 A1 | 3/2014 | McLaughlin et al. |
| 2014/0107786 A1 | 4/2014 | Geisler et al. |
| 2014/0156006 A1 | 6/2014 | Bannigan et al. |
| 2014/0222151 A1 | 8/2014 | Refai et al. |

OTHER PUBLICATIONS

International Search Report for PCT/US2016/020209 dated Jul. 25, 2016.
Written Opinion for PCT/US2016/020209 dated Jul. 25, 2016.

* cited by examiner

EXPANDABLE VERTEBRAL BODY REPLACEMENT DEVICE AND METHOD

FIELD OF THE INVENTION

The present invention relates generally to a medical implant for insertion in a space between a patient's vertebrae. More specifically, but not exclusively, the present invention concerns expandable vertebral body replacement devices for implantation in a patient's spine between the vertebrae.

BACKGROUND OF THE INVENTION

Trauma or disease, such as, tumors may cause pressure on a patient's spinal cord. In order to alleviate the pressure and likely the pain it is causing, surgeons may remove part or all of a patient's vertebral bodies and adjacent vertebral discs in the location of the pressure, during a procedure such as a corpectomy. Often implants are used to replace the removed vertebral bodies to maintain the space between the remaining vertebral bodies.

SUMMARY OF THE INVENTION

Aspects of the present invention provide expanding vertebral body replacement devices for implantation in a patient's spine between the vertebrae and methods of using the same.

In one aspect, provided herein is a vertebral body device, including a body with a first end and a second end, a first rotating member rotatably coupled to the first end, a second rotating member rotatably coupled to the second end, a first extension member moveably coupled to the first end, and a second extension member moveably coupled to the second end.

In another aspect, provided herein is an expandable cage system including a vertebral body device and an insertion instrument. The vertebral body device including a body with a first end and a second end, a first rotating member coupled to the first end, a second rotating member coupled to the second end, a first extension member moveably coupled to the first end, and a second extension member moveably coupled to the second end. The body including a plurality of apertures positioned around the body along a midpoint between the first end and the second end, each of the plurality of apertures spaced apart from the adjacent apertures, a plurality of first positioning holes positioned superior to each of the plurality of apertures, and a plurality of second positioning holes positioned inferior to each of the plurality of apertures. The plurality of apertures, the plurality of first positioning holes, and the plurality of second positioning holes being sized to receive the insertion instrument.

In yet another aspect, provided here is a method for using an expandable cage system, including obtaining a vertebral body device and an insertion instrument. The vertebral body device including a body with a first end and a second end, a first rotating member rotatably coupled to the first end, a second rotating member rotatably coupled to the second end, a first extension member moveably coupled to the first end, and a second extension member moveably coupled to the second end. The method also includes coupling the vertebral body device to the insertion instrument and inserting the vertebral body device into a patient between two vertebral bodies. The method further includes expanding the vertebral body device and removing the insertion instrument. Finally, the method includes closing the patient.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Figure 1:
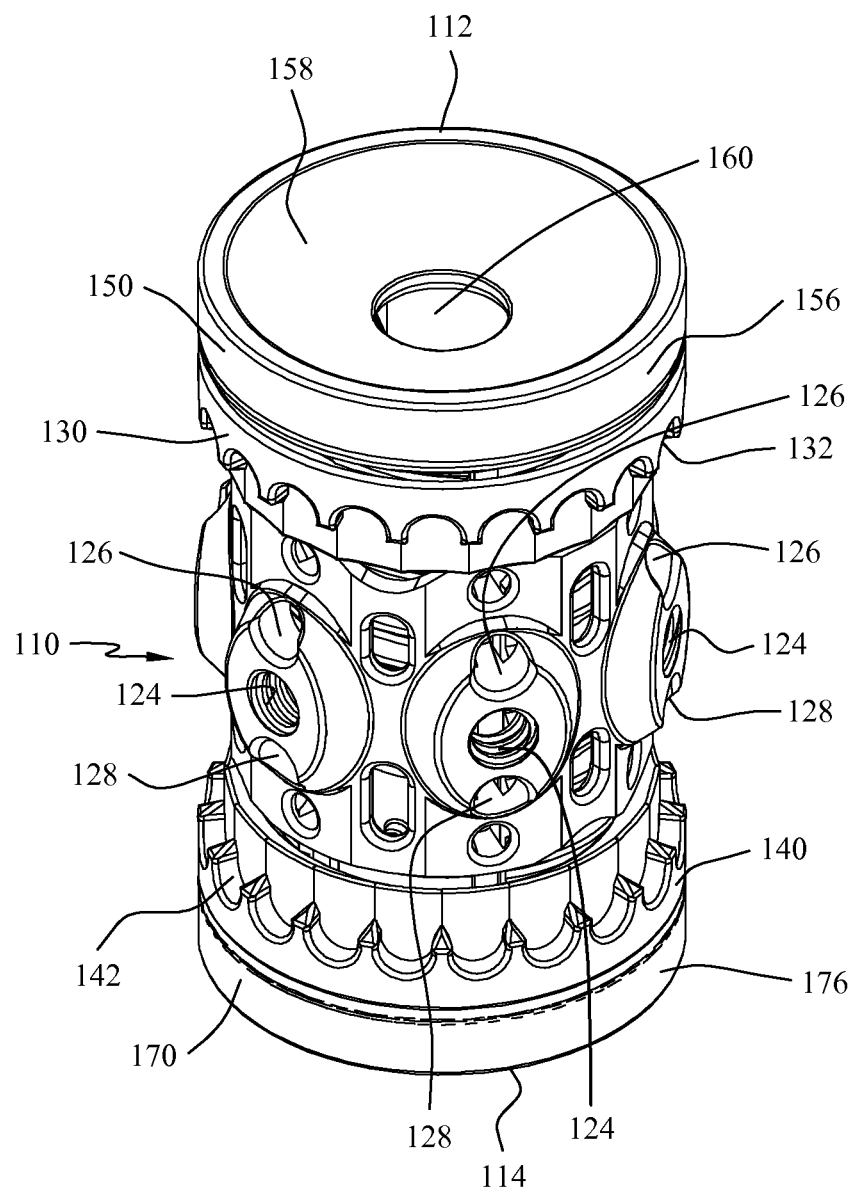
FIG. 1 is a top perspective view of a vertebral body device, in accordance with an aspect of the present invention.
Figure 2:
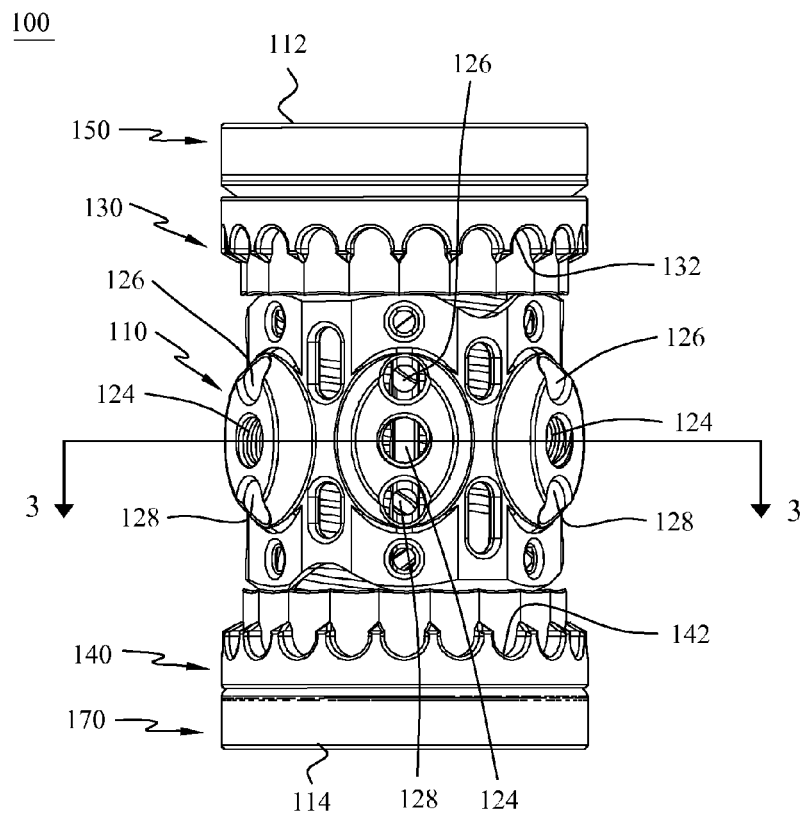
FIG. 2 is a side view of the vertebral body device of FIG. 1, in accordance with an aspect of the present invention.
Figure 3:
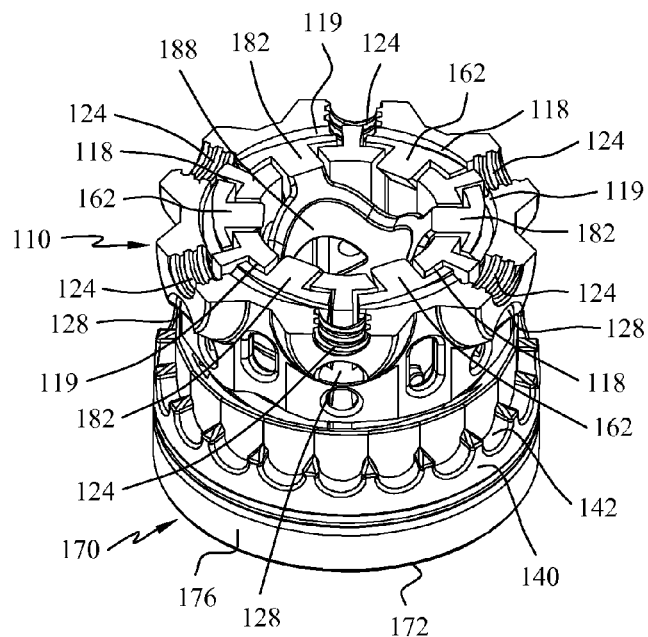
FIG. 3 is a cross-sectional view of the vertebral body device of FIG. 1 taken along line 3-3 in FIG. 2, in accordance with an aspect of the present invention.

Generally stated, disclosed herein is an expandable vertebral body replacement device. Further, methods of assembling and using the expandable vertebral body replacement device are discussed.

In this detailed description and the following claims, the words proximal, distal, anterior, posterior, medial, lateral, superior, inferior, cephalad, and caudal are defined by their standard usage for indicating a particular part of a bone or implant according to the relative disposition of the natural bone or directional terms of reference. For example, "proximal" means the portion of an implant nearest the insertion instrument, while "distal" indicates the portion of the implant farthest from the insertion instrument. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above, "inferior" means a direction below another object or structure, "cephalad" means a direction toward the head, and "caudal" means a direction toward the inferior part of the body.

Referring to the drawings, wherein like reference numerals are used to indicate like or analogous components throughout the several views, and with particular reference to FIGS. 1-5, there is illustrated an exemplary embodiment of an expandable vertebral body replacement device 100. The terms "expandable vertebral body replacement device," "vertebral body device," "device," "expandable cage," and "cage" may be used interchangeably herein as they essentially describe the same type of device. The vertebral body device 100 may include a body 110, a first rotating member 130 rotatably coupled to the first end 112 of the body 110, a second rotating member 140 rotatably coupled to the second end 114 of the body 110, a first extension member 150 moveably coupled to a first end 112 of the body 110, and a second extension member 170 moveably coupled to a second end 114 of the body 110.

Figure 8:
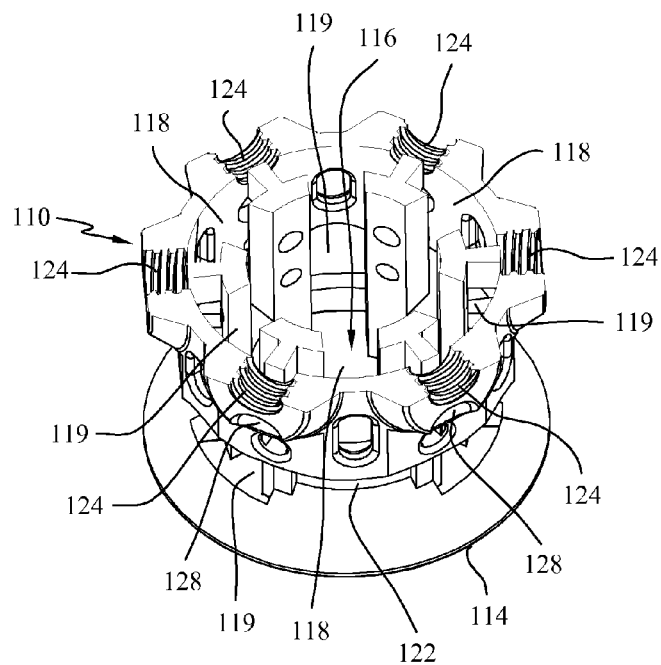
FIG. 8 is a perspective cross-sectional view of the body of FIG. 6 taken along line 8-8 in FIG. 7, in accordance with an aspect of the present invention.
Figure 9:
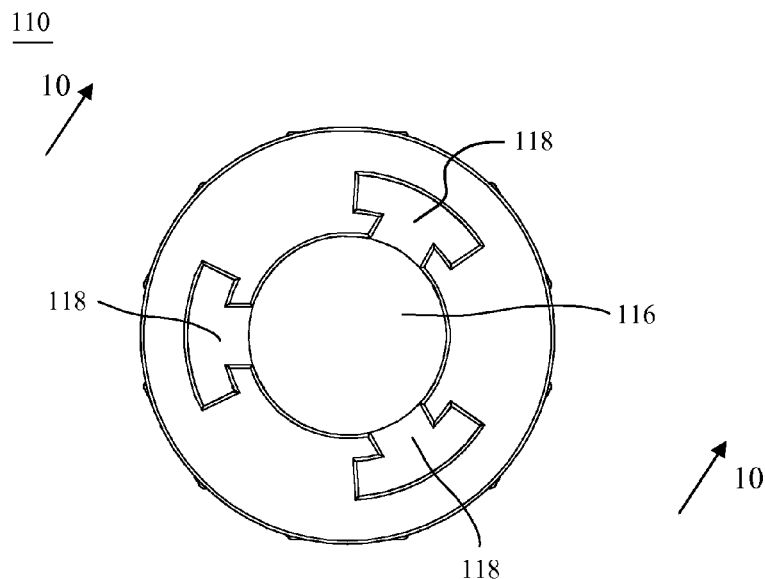
FIG. 9 is a top view of the body of FIG. 6, in accordance with an aspect of the present invention.
Figure 10:
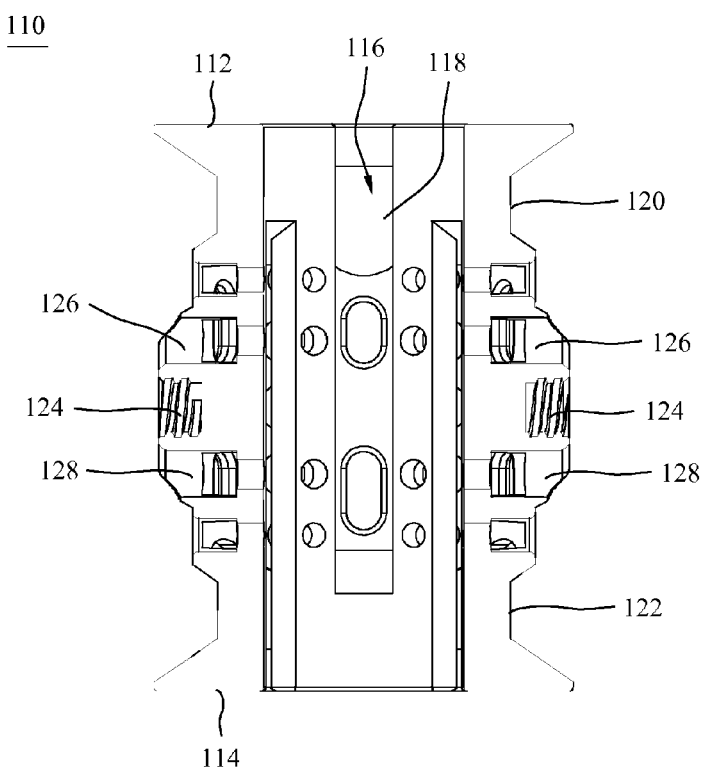
FIG. 10 is a cross-sectional view of the body of FIG. 6 taken along line 10-10 in FIG. 9, in accordance with an aspect of the present invention.

As shown in FIGS. 5, 6, and 8-10, the body 110 may include an opening 116 extending from the first end 112 to the second end 114, for example, along the longitudinal axis of the body 110. The opening 116 may include at least two channels 118, 119 extending into the body 110 from the opening 116. At least one first channel 118 may extend from the first end 112 toward the second end 114 and at least one second channel 119 may extend from the second end 114 toward the first end 112. The channels 118, 119 may be, for example, evenly spaced around the opening 116. As shown, the body 110 may include, for example, three first channels 118 open on the first end 112 and three second channels 119 open on the second end 114. The channels 118, 119 may be spaced evenly apart around the circumference of the opening and may alternate between a first channel 118 and a second channel 119, as shown in FIG. 8. Alternative numbers of channels 118, 119 are also contemplated, for example, the body 110 may include the same number of first channels 118 and second channels 119, more first channels 118 than second channels 119, or more second channels 119 than first channels 118.

The exterior surface of the body 110 may further include a first groove 120 near the first end 112 and a second groove 122 near the second end 114, as shown in FIGS. 4-7 and 10. The first and second grooves 120, 122 may extend around the circumference of the body 110 and be sized to receive the first and second rotating members 130, 140, respectively. The first groove 120 may extend into the first channels 118 to enable the first rotating member 130 to engage the first extension member 150 and the second groove 122 may extend into the channels 119 to enable the second rotating member 140 to engage the second extension member 170. As shown in FIGS. 1-8 and 10, the body 110 may also include a plurality of apertures 124 positioned around the circumference of the exterior surface. The plurality of apertures 124 may be positioned, for example, at a midpoint between the first end 112 and second end 114 of the body 110. The plurality of apertures 124 may be, for example, threaded openings. The body 110 may also include a plurality of first positioning holes 126 superior to the plurality of apertures 124 and a plurality of second positioning holes 128 inferior to the plurality of apertures 124.

Figure 4:
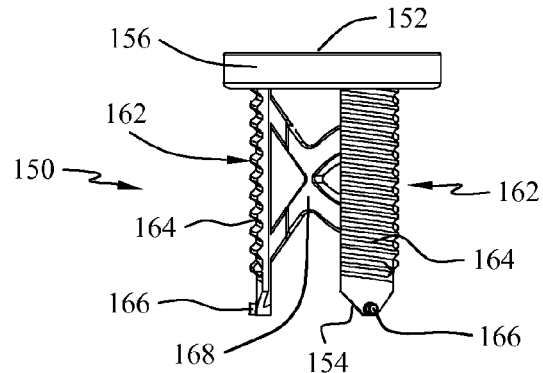
FIG. 4 is an exploded side view of the vertebral body device of FIG. 1, in accordance with an aspect of the present invention.
Figure 4:
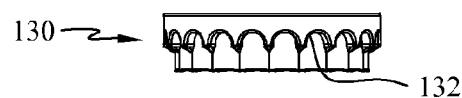
Figure 4:
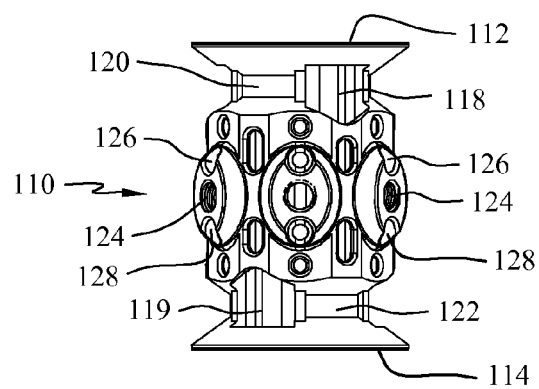
Figure 4:
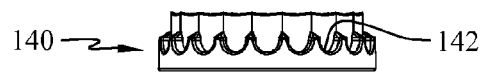
Figure 4:
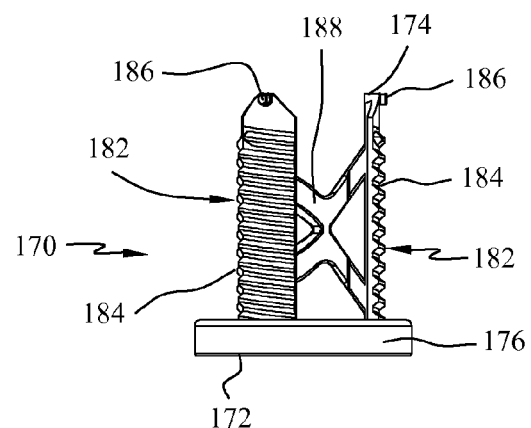
Figure 5:
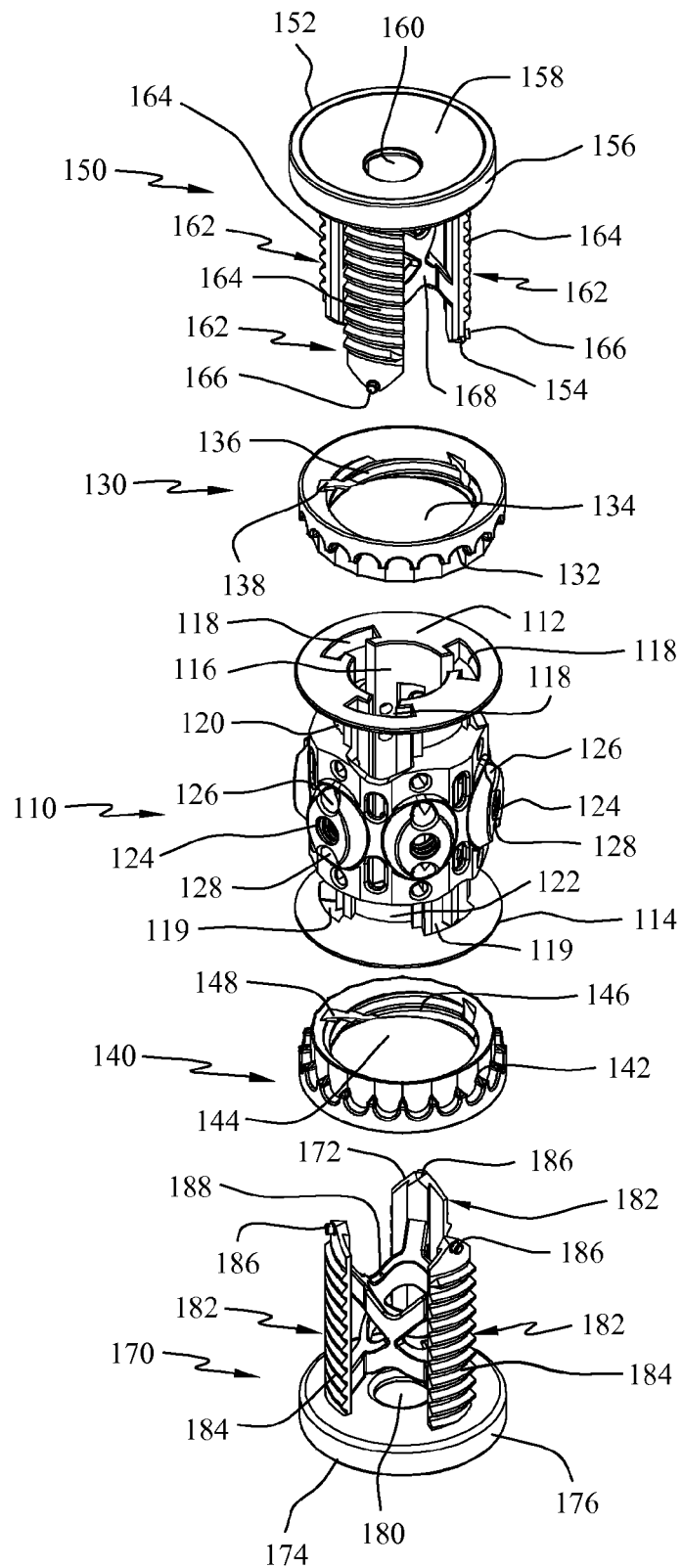
FIG. 5 is an exploded perspective view of the vertebral body device of FIG. 1, in accordance with an aspect of the present invention.
Figure 6:
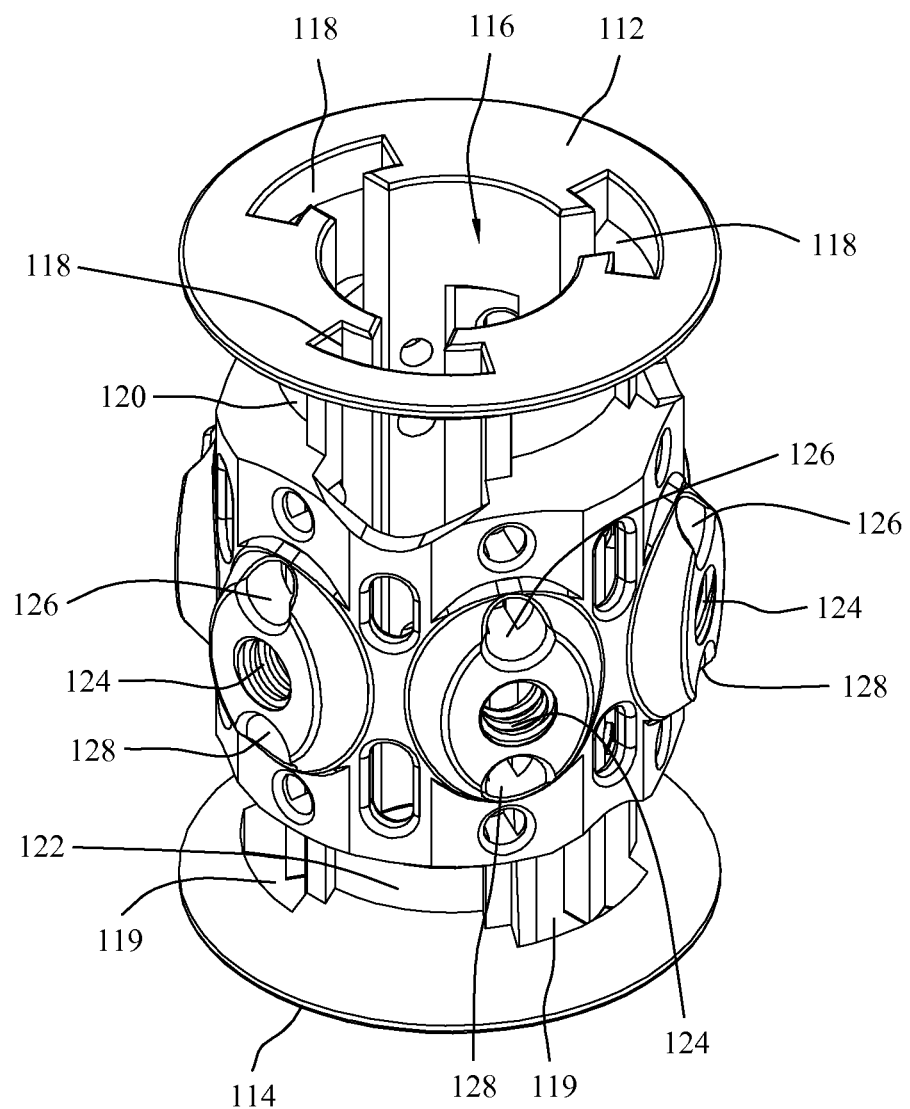
FIG. 6 is a top perspective view of a body of the vertebral body device of FIG. 1, in accordance with an aspect of the present invention.
Figure 7:
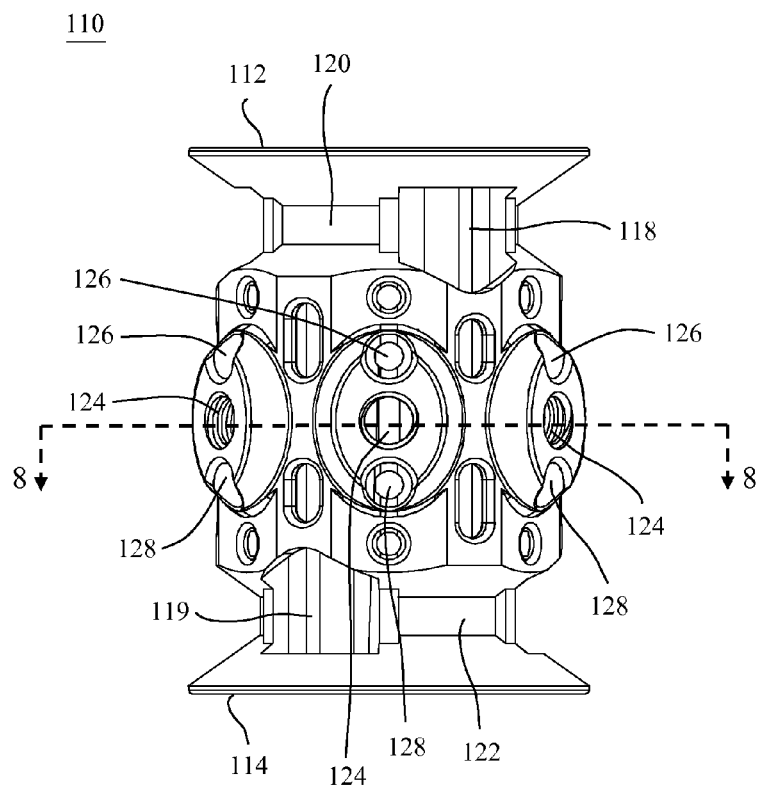
FIG. 7 is a side view of the body of FIG. 6, in accordance with an aspect of the present invention.
Figure 11:
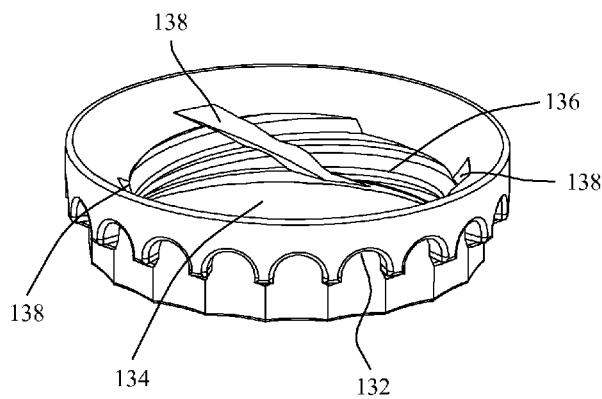
FIG. 11 is a top perspective view of a rotating member of the vertebral body device of FIG. 1, in accordance with an aspect of the present invention.
Figure 12:
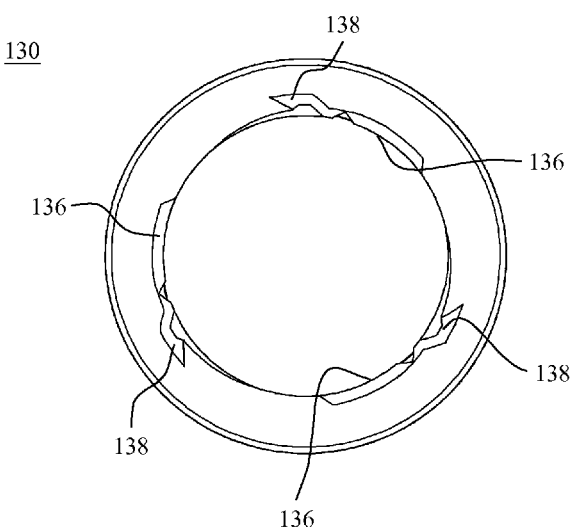
FIG. 12 is a top view of the rotating member of FIG. 11, in accordance with an aspect of the present invention.
Figure 13:
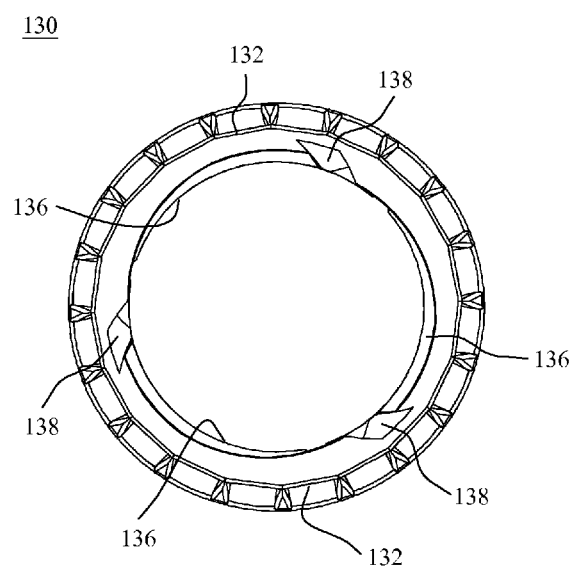
FIG. 13 is a bottom view of the rotating member of FIG. 11, in accordance with an aspect of the present invention.
Figure 14:
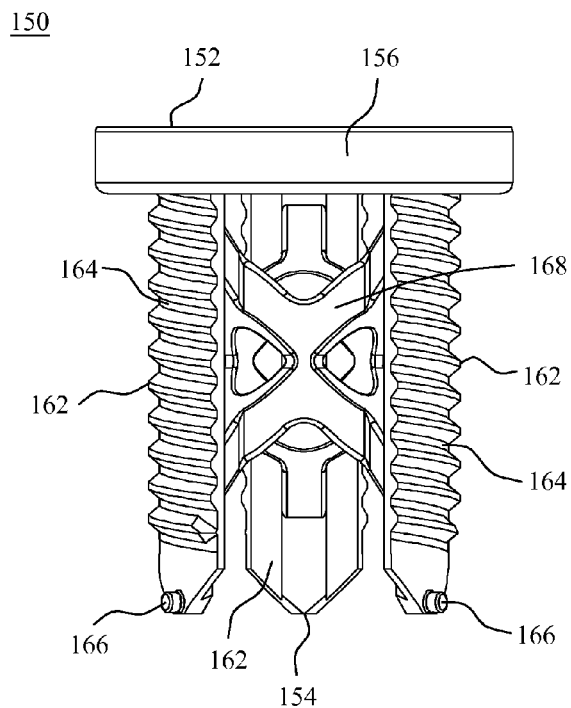
FIG. 14 is a side view of an extension member of the vertebral body device of FIG. 1, in accordance with an aspect of the present invention.

The first rotating member 130 is shown in FIGS. 1-2, 4-5, and 11-13. The first rotating member 130 may include a center opening 134 extending through the first rotating member 130. The exterior surface of the first rotating member 130 may include a plurality of grooves, notches, gear teeth, teeth, or scallops 132, as best seen in FIGS. 11 and 13. The plurality of grooves 132 may be, for example, sized to receive an insertion tool, such as tool 200 described in greater detail below. The first rotating member 130 may also include threads 136 on the interior surface of the member 130, as shown in FIGS. 5 and 11. In addition, the first rotating member 130 may include at least one angled slot 138 to receive a portion of the first extension member 150, as shown in FIGS. 11-13.

The second rotating member 140, as shown in FIGS. 4 and 5, may include a plurality of grooves 142, a center opening 144, threads 146, and angled slots 148. The plurality of grooves 142, center opening 144, threads 146, and angled slots 148 may be of the type described above with reference to the plurality of grooves 132, center opening 134, threads 136, and angled slots 138 of first rotating member 130, which will not be described again here for brevity sake.

Figure 15:
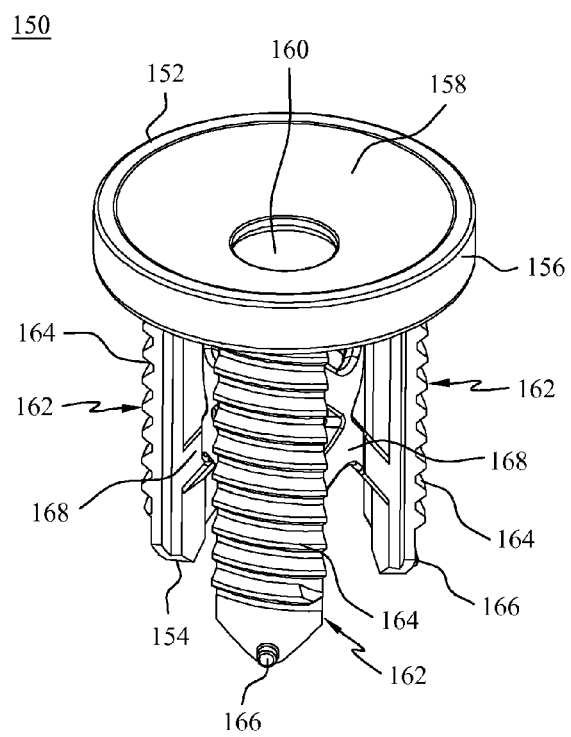
FIG. 15 is a top perspective view of the extension member of FIG. 14, in accordance with an aspect of the present invention.
Figure 16:
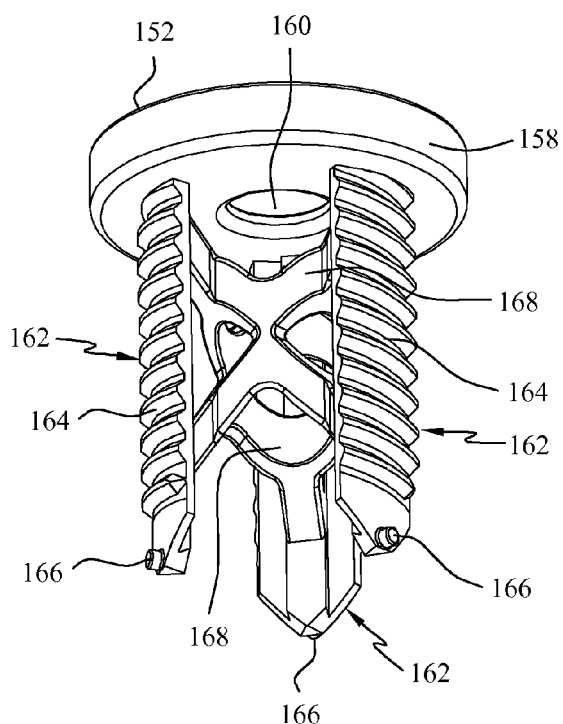
FIG. 16 is a bottom perspective view of the extension member of FIG. 14, in accordance with an aspect of the present invention.
Figure 17:
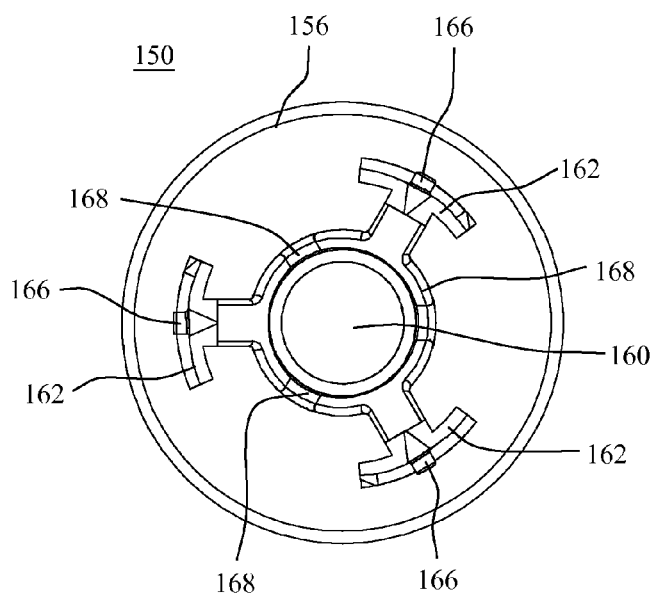
FIG. 17 is a bottom view of the extension member of FIG. 14, in accordance with an aspect of the present invention.
Figure 18:
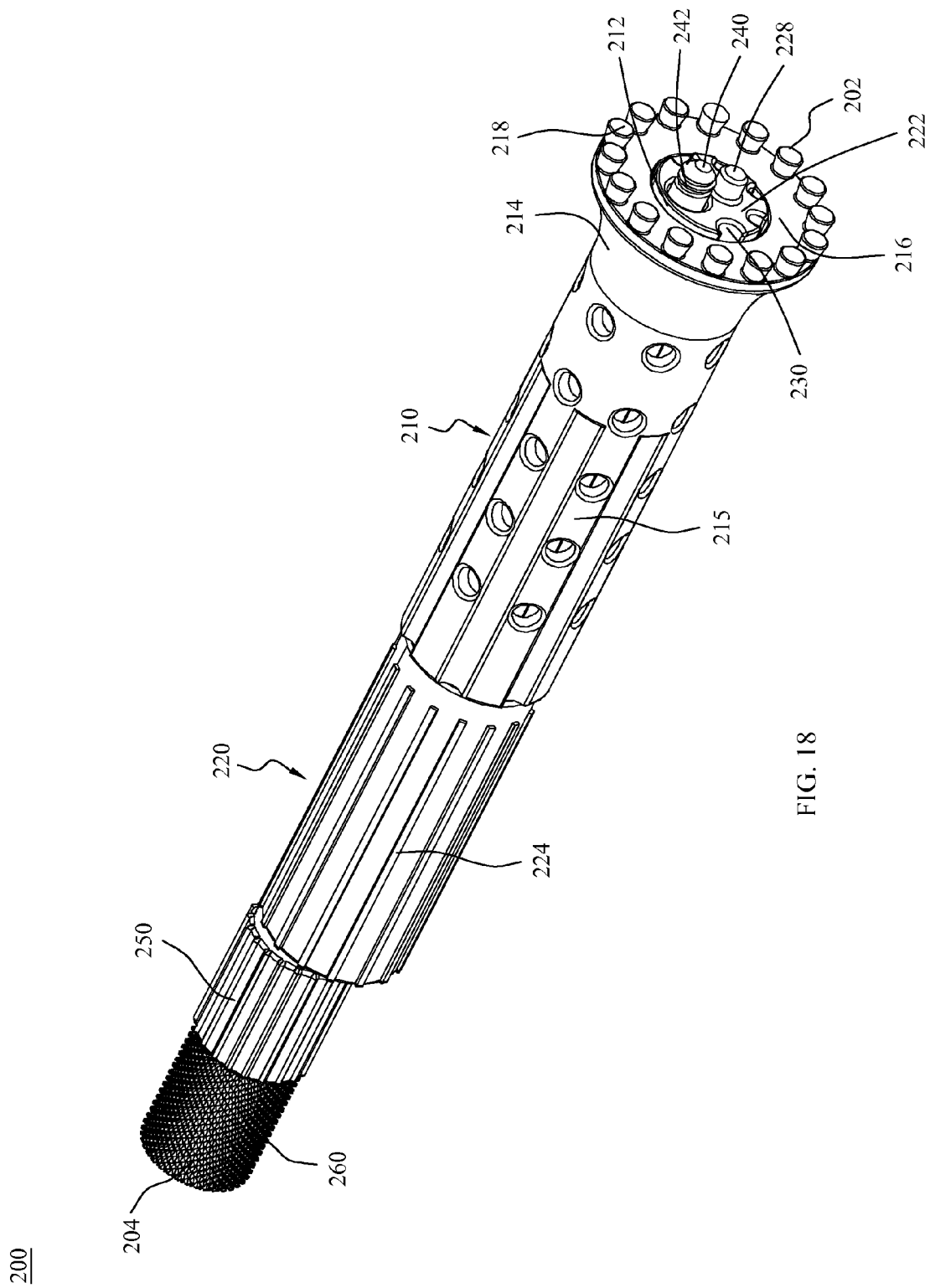
FIG. 18 is a perspective view of an insertion tool for the vertebral body device of FIG. 1, in accordance with an aspect of the present invention.
Figure 19:
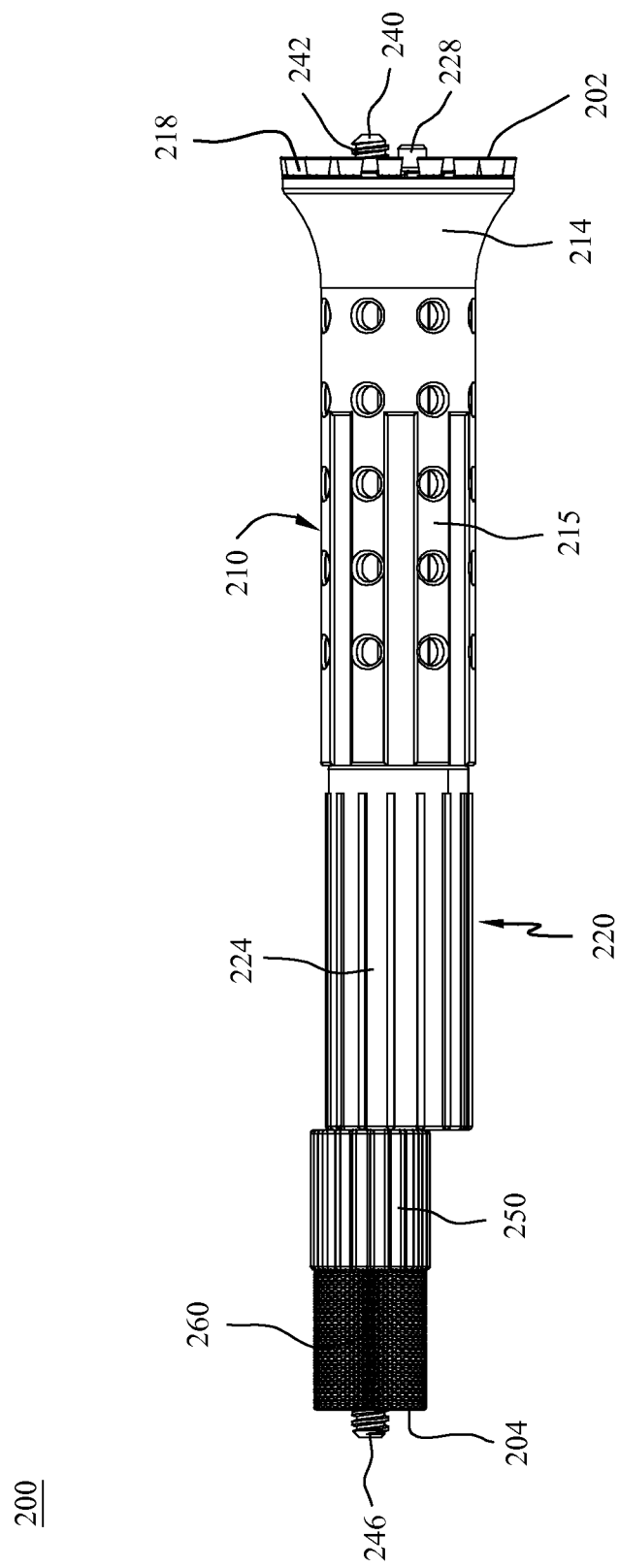
FIG. 19 is a side view of the insertion tool of FIG. 18, in accordance with an aspect of the present invention.

As shown in FIGS. 4-5 and 14-17, the first extension member 150 may include a first end 152 and a second end 154. The first extension member 150 may also include a top portion or first end cap 156 at the first end 152 and at least one leg member 162 extending away from the top portion 156 and to the second end 154. The top portion 156 may include a curved top surface 158, for example, a hemispherical or cylindrical shaped cup, and a center opening 160, as shown in FIGS. 5 and 15. The curved top surface 158 and center opening 160 may be configured to receive autologous bone graft or allograft material which will contact and allow for fusion with the adjacent vertebral bodies and additional graft material positioned between the at least one leg member 162. The curved surface 158 may be, for example, sized to allow the graft material to be positioned within the first extension member 150 to minimize the height. In addition, the hemispherical shaped cup may be selected, for example, to minimize the amount of graft material necessary to fill the curved surface 158. The top surface 158 may be, for example, coated, textured, porous, or of a trabecular metal nature to allow for bone growth into the first extension member 150 after implantation. In an alternative embodiment, it is also contemplated that the curved top surface 158 may be, for example, a mesh or open slotted top surface to allow for the bone graft material positioned in the top portion 156 to make contact with bone graft material positioned between the at least one leg member 162. The top portion 156 may also be configured to receive, for example, end caps (not shown) with lordosis or a larger footprint to contact larger adjacent vertebral bodies at the outer ring of their end plates.

The at least one leg member 162 may be, for example, three leg members 162. The leg members 162 may include threads 164 on an exterior surface and a tab 166 positioned at the second end 154 of the first extension member 150. The second end 154 of the leg members 162 may be, for example, tapered or angled and the tab 166 may be positioned at the tip of the tapered or angled end. The tabs 166 may be sized and shaped to engage the angled slots 138 on the interior surface of the first rotating member 130. As the tabs 166 are translated within the slots 138 of the first rotating member 130, the threads 164 of the leg members 162 engage the interior threads 136 of the first rotating member 130 to couple the first extension member 150 to the first rotating member 130. The leg members 162 may be curved to enable the leg members 162 to rotate with respect to the first rotating member 130. The first extension member 150 may also include support members 168 positioned between and connected to the leg members 162. The support members 168 may be, for example, cross-hatching braces positioned in rings. As depicted in FIGS. 14-17, the support members 168 may, for example, extend out from the back side of the leg members 162 and be connected between the leg members 162 in crisscross or "X" shaped arrangements. The crisscross arrangement of the leg members 162 may be, for example, curved between the leg members 162 to form a ring-like shape.

The second extension member 170, as shown in FIGS. 4 and 5, may include a first end 172 and a second end 174. The second extension member 170 may also include a bottom portion or second end cap 176 at the first end 172 and at least one leg member 182 extending away from the bottom portion 176 and to the second end 174. The bottom portion 176 may include a curved bottom surface 178 and an opening 180. The curved bottom surface 178 may be of the type described above with respect to the curved top surface 158, which will not be described again here for brevity sake. The curved bottom surface 178 and center opening 180 may also be configured to receive autologous bone graft or allograft material as described in greater detail above with respect to the first extension member 150.

The at least one leg member 182 may be, for example, three leg members 182 and may include threads 184, tabs 186, and support members 188. The threads 184, tabs 186, and support members 188 may be of the type described above with reference to threads 164, tabs 166, and support members 168, which will not be described again here for brevity sake. The tabs 186 may be sized and shaped to engage the angled slots 148 on the interior surface of the second rotating member 140. As the tabs 186 are translated within the slots 148 of the second rotating member 140, the threads 184 of the leg members 182 engage the interior threads 146 of the first rotating member 140 to couple the second extension member 170 to the second rotating member 140. The leg members 182 may be curved to enable the leg members 182 to rotate with respect to the second rotating member 140.

The vertebral body replacement device 100 may be assembled by obtaining a body 110 with a first rotating member 130 positioned in the first groove 120 and a second rotating member 140 positioned in the second groove 122. Next, the first and second extension members 150, 170 may be inserted into the channels 118 in the opening 116 of the body 110. The first extension member 150 may be inserted into the channels 118 from the first end 112. During insertion into the channels 118, the tabs 166 of the first extension member 150 may be aligned with the angled slots 138 on the interior surface of the first rotating member 130. The tabs 166 may be translated within the angled slots 138 by rotating the first extension member 150 until the threads 164 of the leg members 162 engage the interior threads 136 of the first rotating member 130. The first extension member 150 may be rotated until the member 150 engages the first end 112 of the body 110. Once the first extension member 150 is positioned in the body 110, then, the second extension member 170 may be inserted into the opening 116. The second extension member 170 may be inserted into the channels 119 from the second end 114. During insertion into the channels 119, the tabs 186 of the second extension member 170 may be aligned with the angled slots 148 on the interior surface of the second rotating member 140. The tabs 186 may be translated within the angled slots 148 by rotating the second extension member 170 until the threads 184 of the leg members 182 engage the interior threads 146 of the second rotating member 140. The second extension member 170 may be rotated until the member 170 engages the second end 114 of the body 110.

Referring now to FIGS. 18-23, an insertion instrument or inserter tool 200 is shown. The tool 200 includes a first end 202 and a second end 204. The tool 200 may include a deployment handle 210 at the first end 202, a position selector member 220 rotatably coupled to the handle 210, a rod 240 extending through the member 220, an implant attachment member 250 coupled to a portion of the rod 240, and a tension adjustment member 260 at the second end 204 and rotatably coupled to the rod 240.

Figure 22:
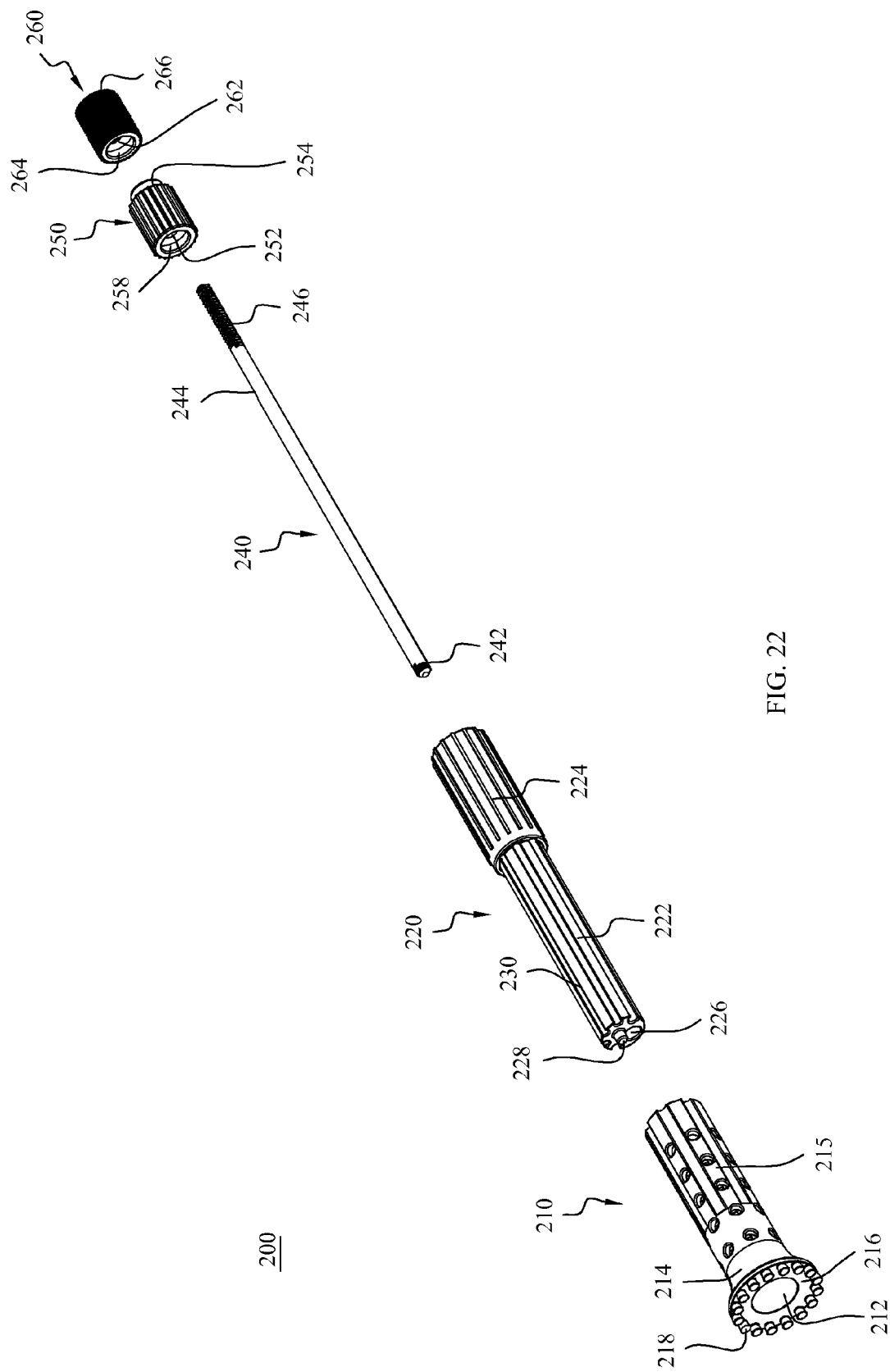
FIG. 22 is an exploded view of the insertion tool of FIG. 18 from a first end, in accordance with an aspect of the present invention.
Figure 23:
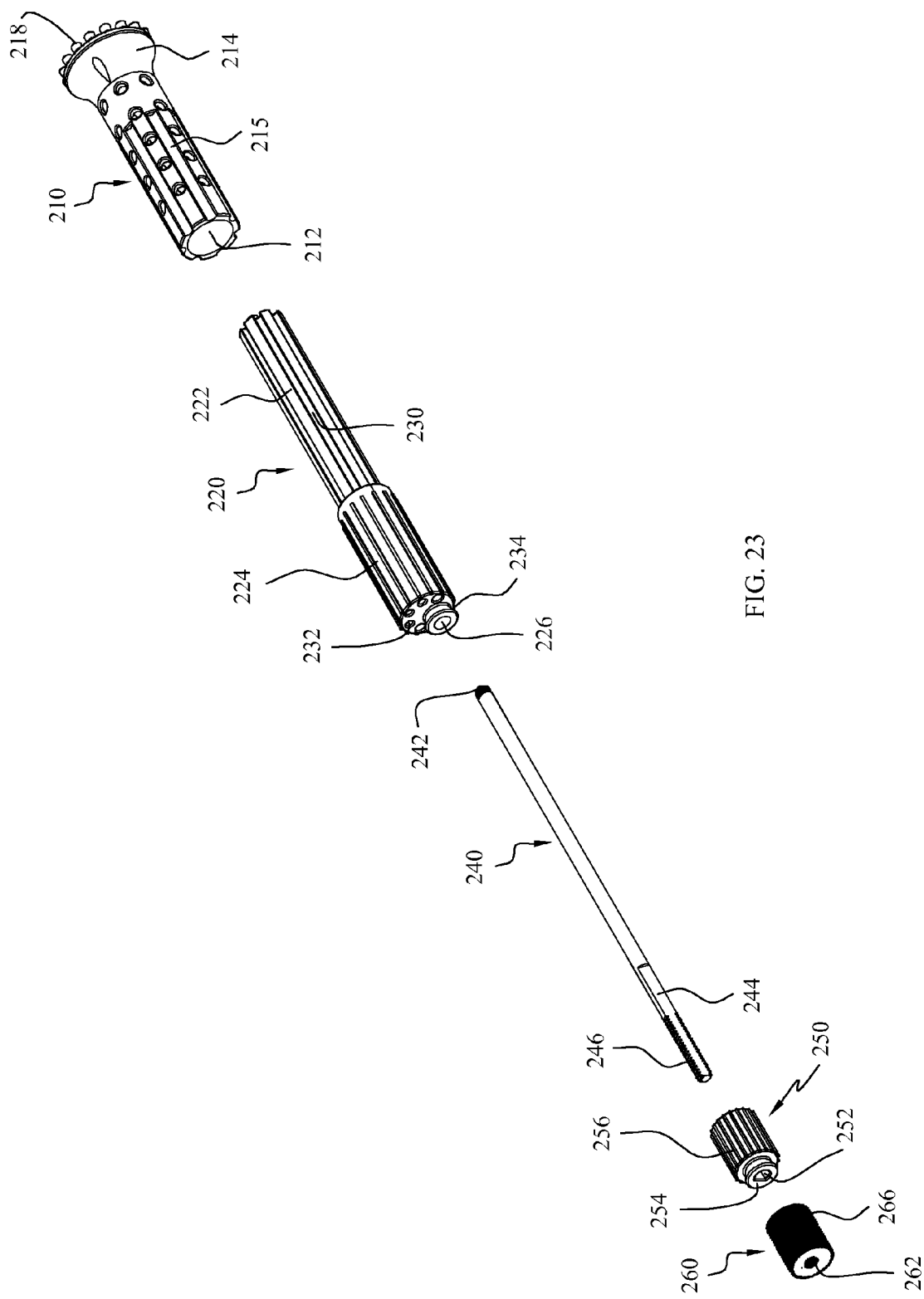
FIG. 23 is an exploded view of the insertion tool of FIG. 18 from a second end, in accordance with an aspect of the present invention.

As shown in FIGS. 22 and 23, the deployment handle 210 may include a passageway 212 extending along the longitudinal axis of the handle 210 from a first end to a second end. The handle 210 may also include a neck 214 near the first end. The neck 214 may, for example, increase the diameter of the handle from a body portion 215 to the engagement end 216. The engagement end 216 may include a plurality of projections 218 for engaging the grooves 132, 142 in the rotating members 130, 140. The plurality of projections 218 may be, for example, cone shaped or angled toward the point of attachment with the handle 210 to allow for the projections 218 to engage the grooves or teeth 132, 142 of the rotating members 130, 140. The teeth 132, 142 may have, for example, an undercut or angled shape to lock the plurality of projections 218 into the teeth 132, 142 and prevent jumping of the projections 218 with respect to the teeth 132, 142 as the handle 210 is rotated.

The position selector member 220 may include a first portion 222, a second portion 224, and an opening 226 extending through the entire member 220, as shown in FIGS. 22 and 23. The opening 226 may be offset from the center of the member 220 and extend in a longitudinal direction. The opening 226 may be configured to receive the rod 240. The first portion 222 may also have, for example, a smaller diameter than the second portion 224. The first portion 222 may be sized to fit in the passageway 212 of the handle 210. The first portion 222 may further include a pin 228 extending away from a first end of the first portion 222. The pin 228 may be shaped and sized to fit in the first and second positioning holes 126, 128 of a vertebral body device 100. In addition, the first portion 222 may include a plurality of grooves 230 positioned around the exterior surface. The second portion 224 may include a plurality of holes 232 extending through the second portion 224 in a longitudinal direction and aligning with the grooves 230 in the first portion 222. The second portion 224 may also include a flange 234 surrounding the opening 226. The flange 234 may be configured or sized and shaped to be received within the attachment member 250.

FIGS. 22 and 23 show the rod 240. The rod 240 includes a threaded section 242 at a first end and a cutout portion 244 and a threaded portion 246 at a second end. The threaded portion 246 may extend along the rod 240, for example, a shorter, the same, or a longer distance than the length of the cutout portion 244. The cutout portion 244 may be, for example, a flat or planar portion of the circular rod 240. The rod 240 may be inserted into the opening 226 in the position selector member 220 and extend out the first end 202 of the tool 200.

The implant attachment member 250, as shown in FIGS. 22 and 23, may include an opening 252 which may be shaped, for example, to receive the cutout portion 244. The opening 252 may include, for example, a planar portion and a circular portion to correspond to the planar section and circular section of the cutout portion 244 of the rod 240. The opening 252 may extend through the member 250 in a longitudinal direction. A flange 254 may be positioned around the opening 252 at a first end of the member 250. The second end of the member 250 may include a coupling cavity 258 recessed within the member 250. The cavity 258 may be sized to receive the flange 234 extending away from the position selector member 220 to rotatably couple the implant attachment member 250 to the position selector member 220. The attachment member 250 may also include a grooved exterior surface 256. The grooved surface 256 may, for example, assist the user with turning the member 250.

Referring to FIGS. 22 and 23, the tension adjustment member 260 includes an opening 262 extending through the member 260 in a longitudinal direction. The opening 262 may be threaded with threads corresponding to the threads 246 on the rod 240. As shown in FIG. 22, the adjustment member 260 may also include a coupling cavity 264 which is configured or sized and shaped to receive the flange 254 of the attachment member 250 to rotatably couple the attachment member 250 to the adjustment member 260. Further, the adjustment member 260 may have a textured surface 266 on the exterior of the adjustment member 260 to assist with rotation of the member 260 during use.

With continued reference to FIGS. 18-23, the inserter tool 200 may be assembled by inserting the first portion 222 of the position selector member 220 into the opening 212 in the handle 210. The position selector member 220 may be inserted with the pin 228 in a superior or inferior position. Next, the rod 240 may be inserted into the opening 226 in the second portion 224 of the position selector member 220. The opening 252 of the attachment member 250 may be aligned with the cutout portion 244 of the rod 240 and the attachment member 250 may be inserted over the rod 240. The attachment member 250 may be translated down the rod 240 until it engages the second portion 224 of the position selector member 220. Finally, the adjustment member 260 may be threaded onto the threads 246 of the rod 240 until the adjustment member 260 engages the attachment member 250.

Figure 24:
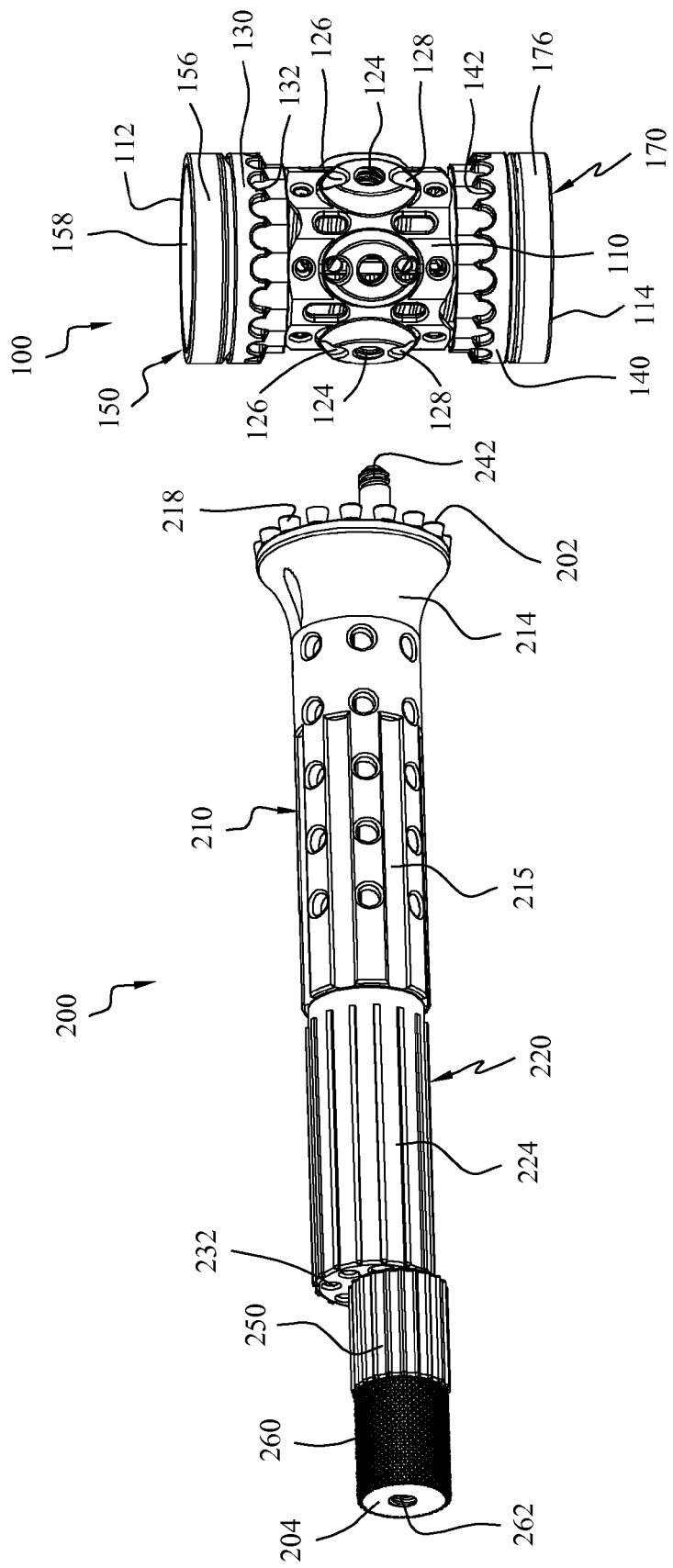
FIG. 24 is a perspective view of a vertebral body device system including the vertebral body device of FIG. 1 and the insertion tool of FIG. 18, in accordance with an aspect of the present invention.

Referring now to FIGS. 24-33 with continued reference to FIGS. 1-23, a method of using the vertebral body device 100 and insertion instrument 200 is shown. The method includes obtaining a vertebral body device 100 and an insertion instrument 200. The vertebral body 100 and insertion instrument 200 may be assembled as described in greater detail above, which will not be described again here for brevity sake. The instrument 200 may then be coupled to the vertebral body device 100 by aligning the threaded section 242 of the rod 240 with one of the plurality of openings 124, as shown in FIG. 24.

Figure 20:
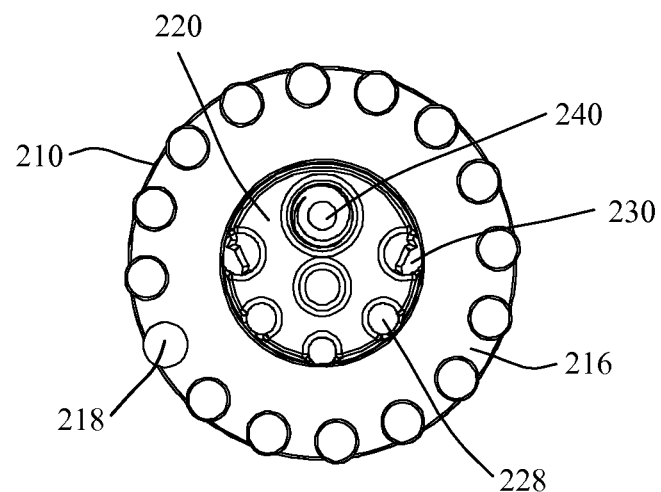
FIG. 20 is a front view of the insertion tool of FIG. 18 in a first position, in accordance with an aspect of the present invention.
Figure 21:
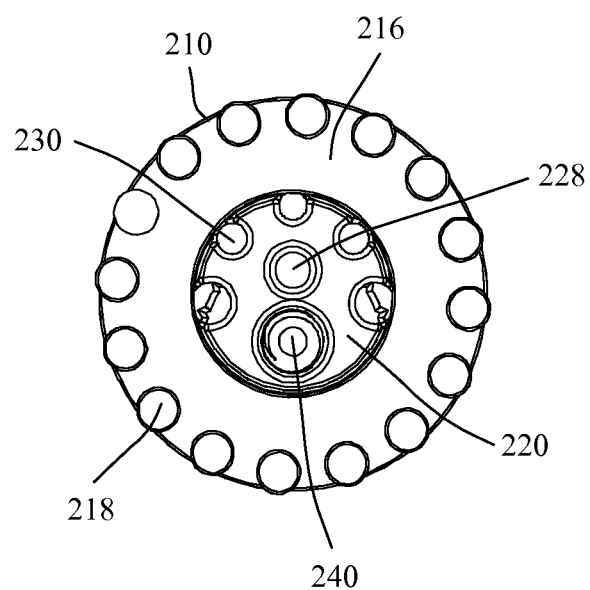
FIG. 21 is a front view of the insertion tool of FIG. 18 in a second position, in accordance with an aspect of the present invention.
Figure 25:
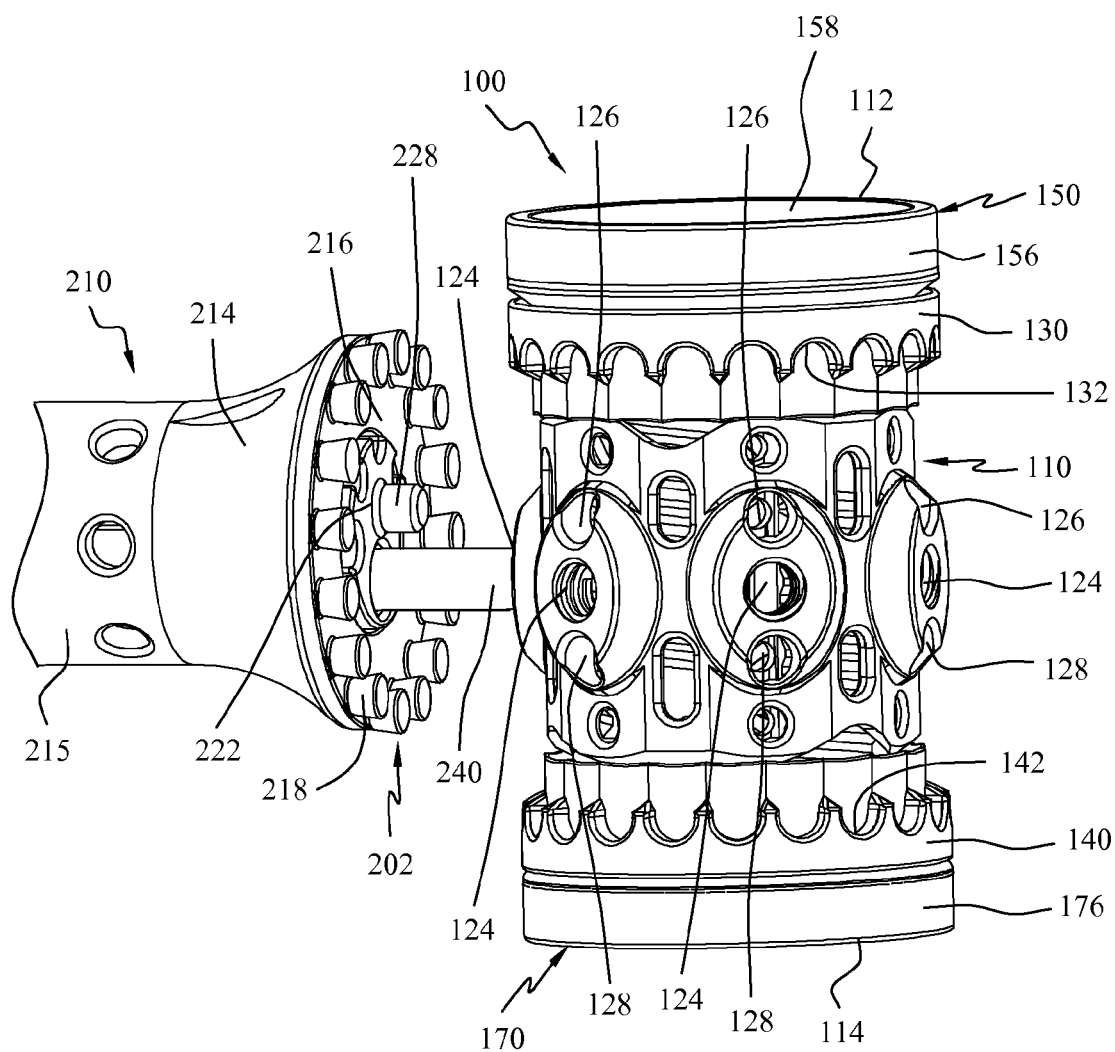
FIG. 25 is a perspective side view of a portion of the system of FIG. 24 with a rod of the tool engaging the vertebral body device, in accordance with an aspect of the present invention.
Figure 26:
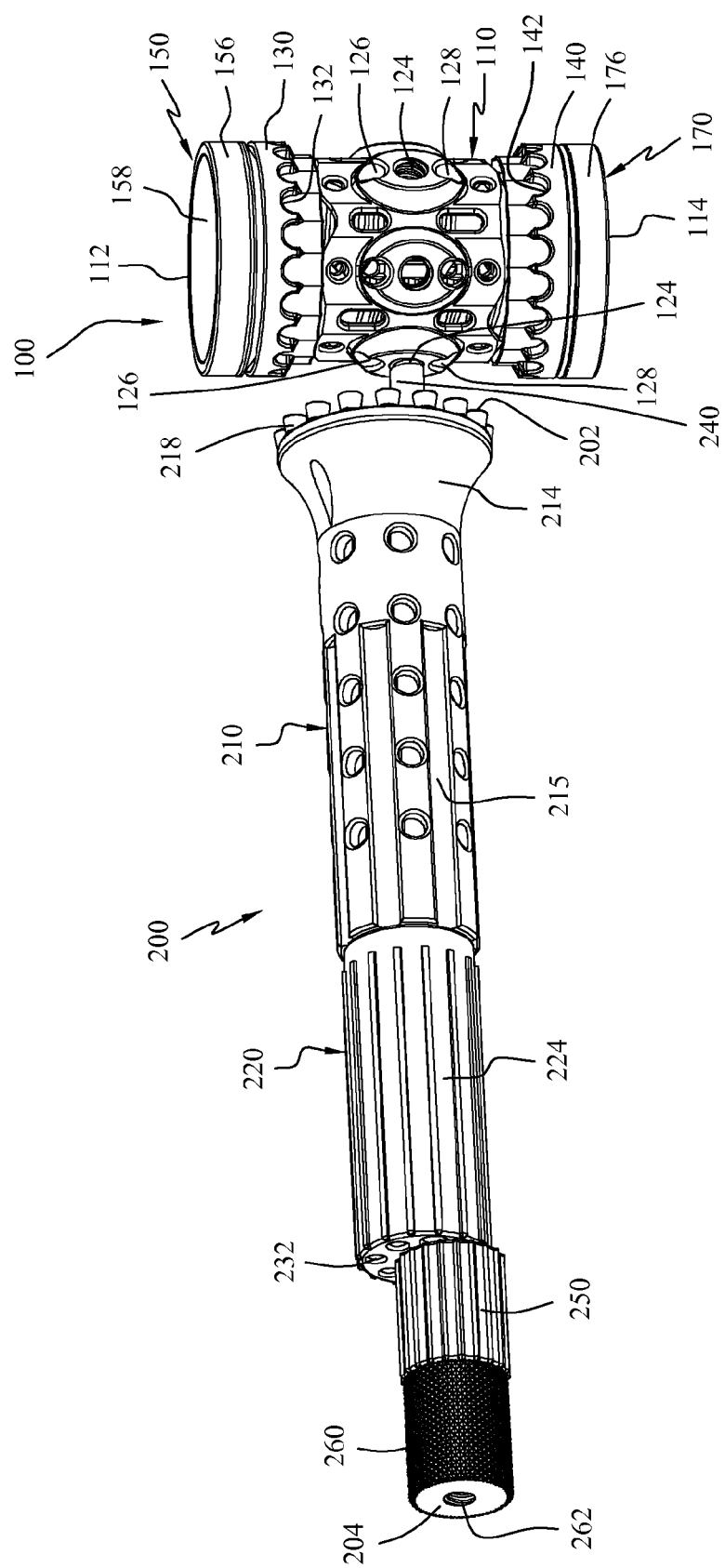
FIG. 26 is a perspective side view of the system of FIG. 24 with a rod of the tool engaging the vertebral body device, in accordance with an aspect of the present invention.
Figure 27:
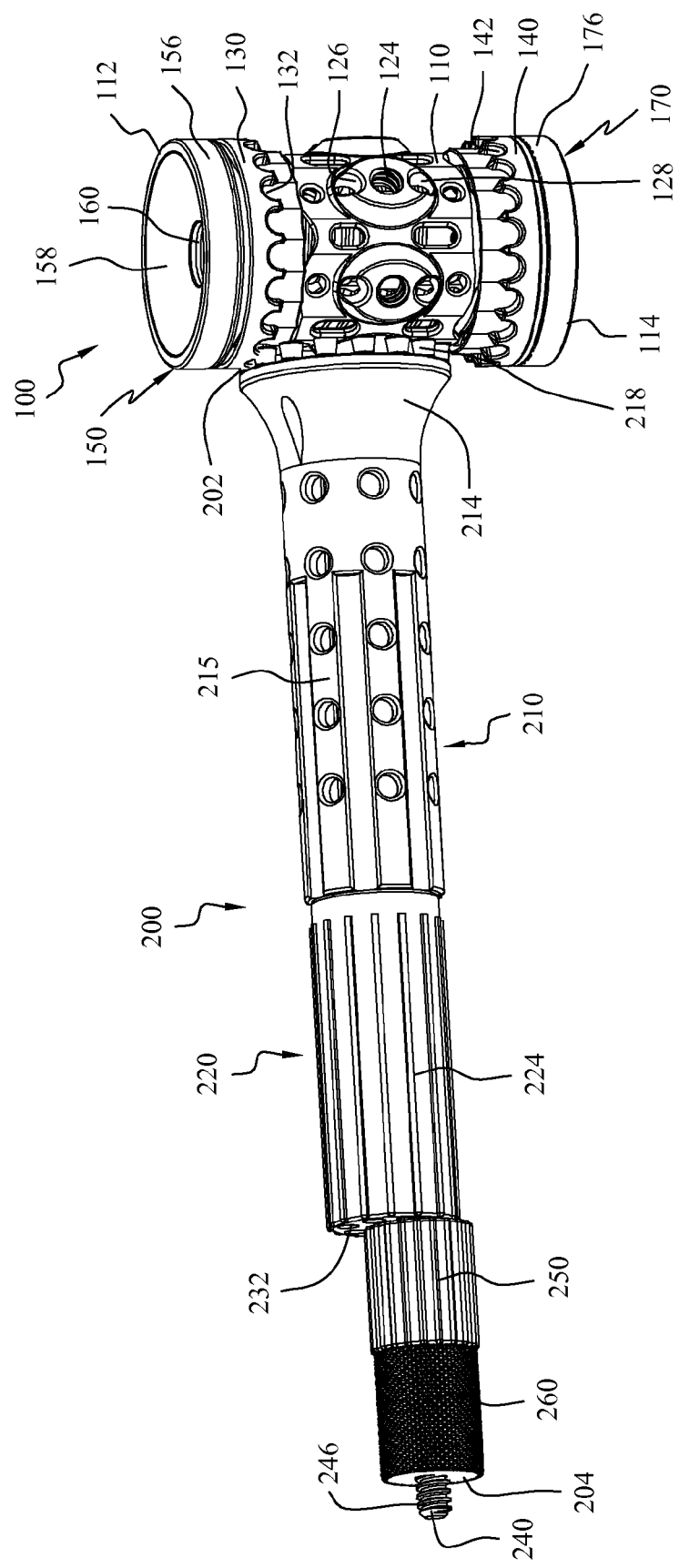
FIG. 27 is a perspective side view of the system of FIG. 24 with the tool engaging the vertebral body device in a first position, in accordance with an aspect of the present invention.
Figure 28:
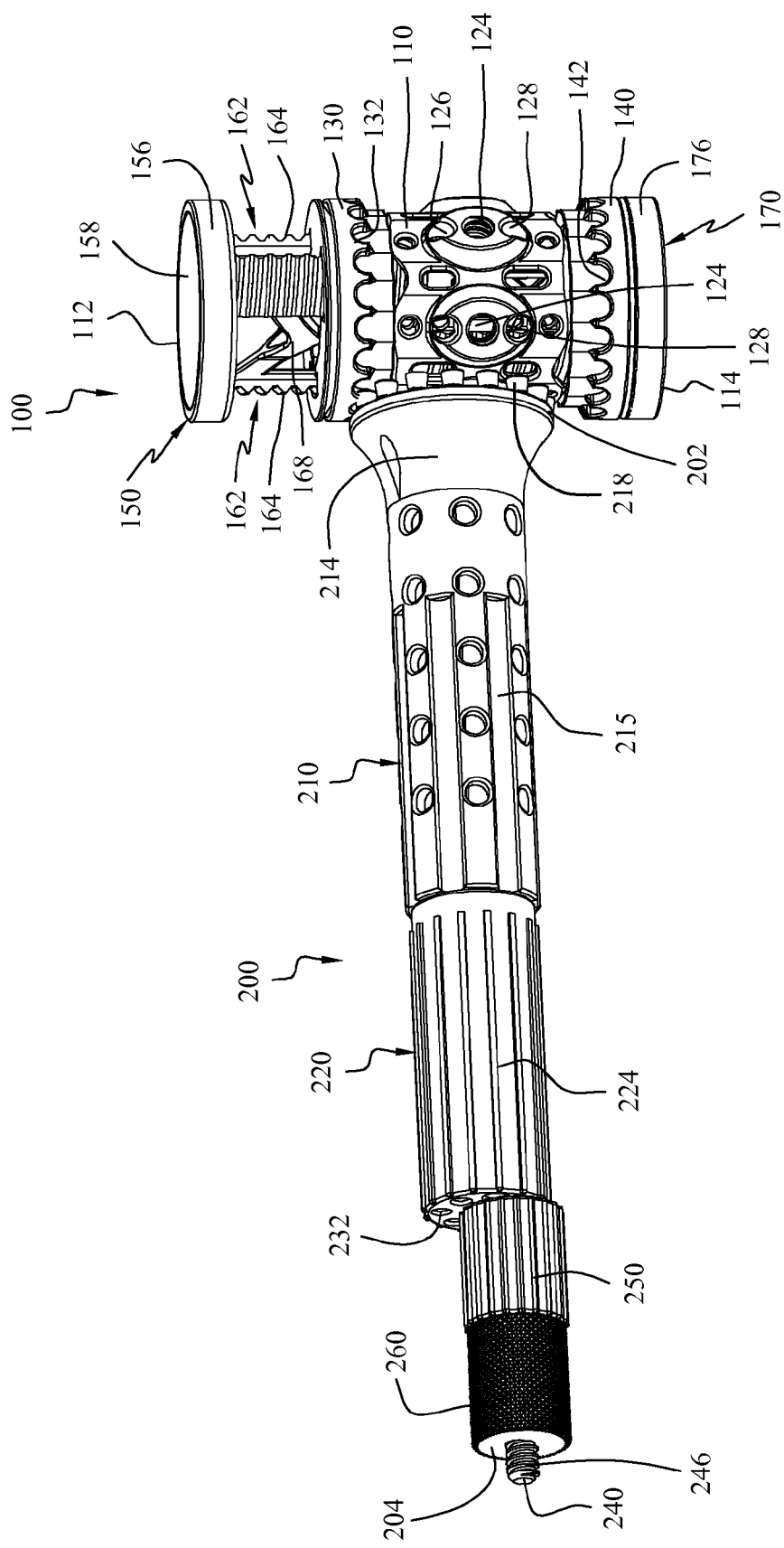
FIG. 28 is a perspective side view of the system of FIG. 24 with the first extension member in a deployed position, in accordance with an aspect of the present invention.

Once aligned the attachment member 250 may be rotated to turn the rod 240 and engage the threaded section 242 with the threads in the selected opening 124, as shown in FIGS. 25 and 26. The attachment member 250 may be, for example, rotated in a clockwise direction to engage the threaded opening 124. Next, the adjustment member 260 may be rotated to translate the deployment handle 210, the position selector member 220, the attachment member 250, and the adjustment member 260 toward the threaded section 242 of the rod 240. The adjustment member 260 translates by the threads in opening 262 engaging the threaded portion 242 of the rod 240. As the adjustment member 260 is rotated the pin 228 is also moved relative to the rod 240 to engage one of the first positioning holes 126 or one of the second positioning holes 128. The pin 228 is shown positioned in a first positioning hole 126 in FIG. 27. FIG. 21 illustrates the pin 228 in a position to engage one of the first positioning holes 126 and FIG. 20 illustrates the pin 228 in a position to engage one of the second positioning holes 128. In addition, as adjustment member 260 is rotated, the plurality of projections 218 on the handle 210 are moved into engagement with the plurality of grooves 132, 142 on the first or second rotating member 130, 140. As shown in FIG. 28, the plurality of projections 218 engage the grooves 132 on the first rotating member 130.

After the pin 228 is positioned in a first positioning hole 126 and projections 218 are positioned in the grooves 132 of the first rotating member 130, the handle 210 may be rotated. As the handle 210 is rotated the projections 218 engage the grooves 132 to rotate the first rotating member 130. As the first rotating member 130 spins, the first extension member 150 may translate in a superior-inferior direction. As shown in FIG. 28, if the handle 210 is rotated in a clockwise direction, the rotating member 130 will spin in a counterclockwise direction, and the first extension member 150 will translate in a superior direction increasing the height of the vertebral body device 100. Alternatively, if the handle 210 is rotated in a counterclockwise direction, the rotating member 130 will spin in a clockwise direction, and the first extension member 150 will translate in an inferior direction decreasing the height of the vertebral body device 100. The amount of superior-inferior translation is limited by the length of the leg members 162.

Figure 29:
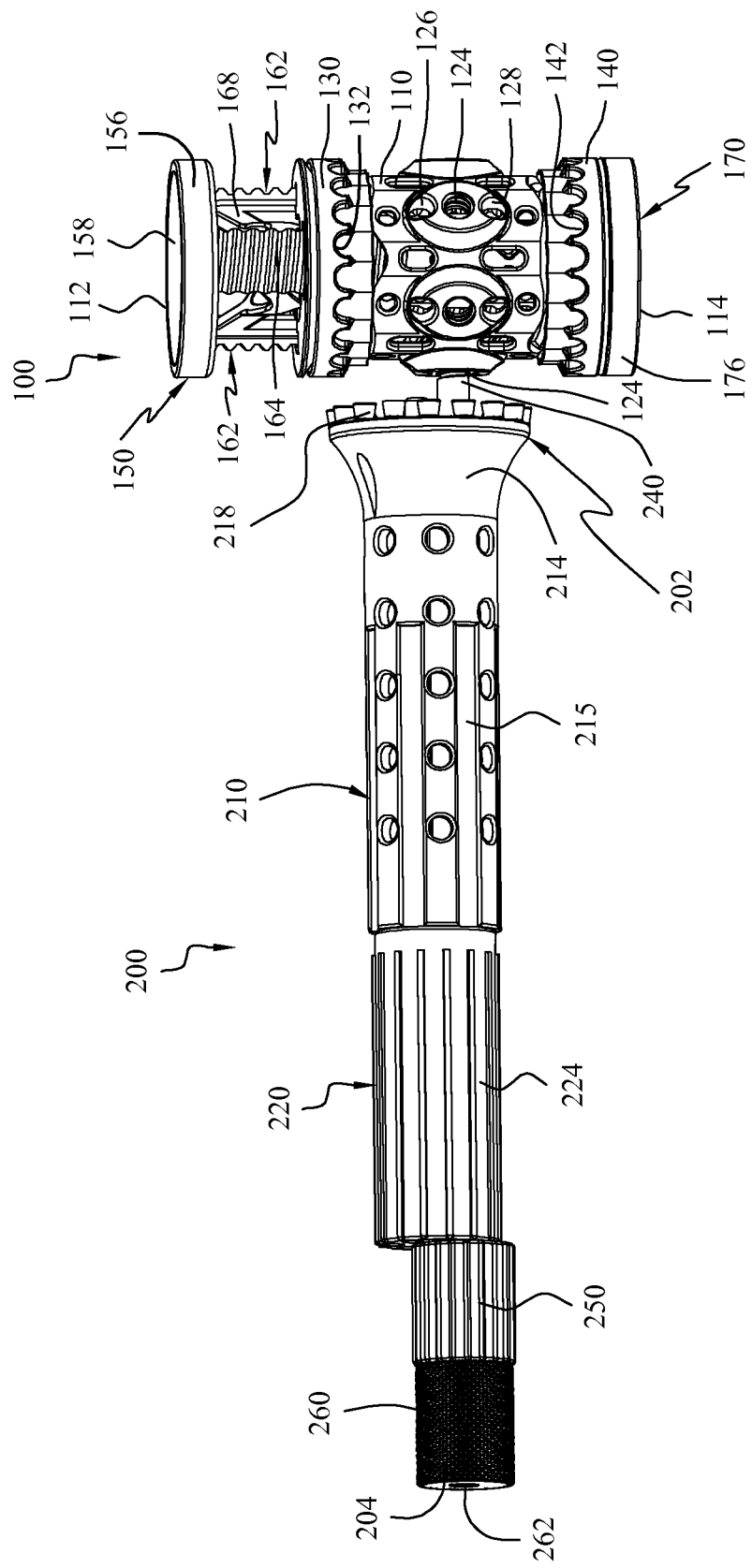
FIG. 29 is a perspective side view of the system of FIG. 24 with the rod of the tool engaging the vertebral body device in a first position, in accordance with an aspect of the present invention.
Figure 30:
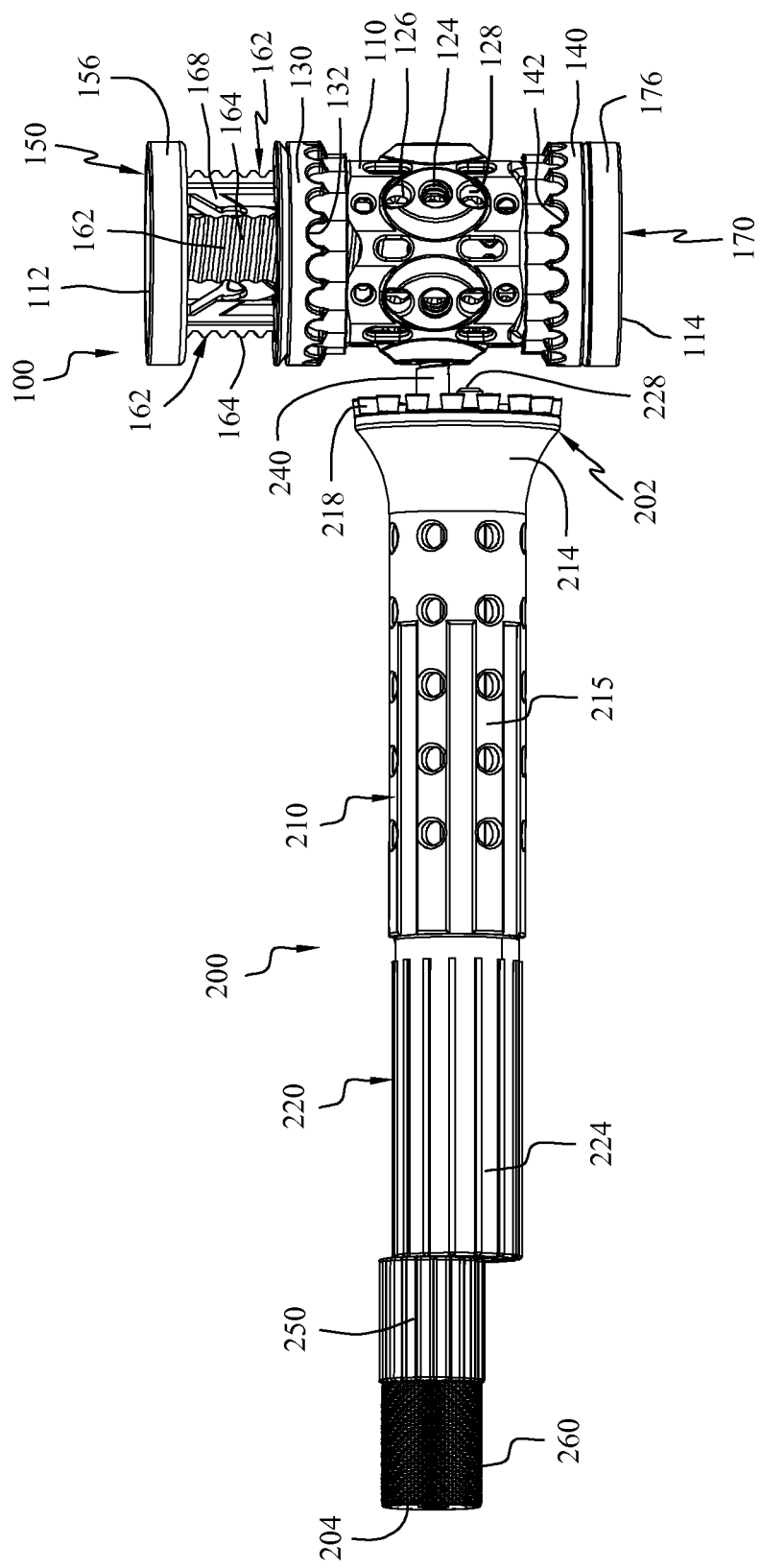
FIG. 30 is a perspective side view of the system of FIG. 24 with the rod of the tool engaging the vertebral body device in a second position, in accordance with an aspect of the present invention.

Once the first extension member 150 is deployed to a desired position, the adjustment member 260 may be rotated in, for example, a counterclockwise direction to disengage the projections 218 from the grooves 132 and the pin 228 from the first positioning hole 126, as shown in FIG. 29. Next, the second extension member 170 may be deployed to a desired position. To deploy the second extension member 170, the position of the pin 228 may be moved to an inferior position. The pin 228 may be moved by holding the attachment member 250 and simultaneously rotating the position selector member 220 to rotate the pin 228 to an inferior position, as shown in FIG. 30. The position selector member 220 may be rotated in a counterclockwise direction to rotate the pin 228 from a superior position to an inferior position and vice versa. The pin 228 may be rotated until it is aligned with one of the second positioning holes 128.

Figure 31:
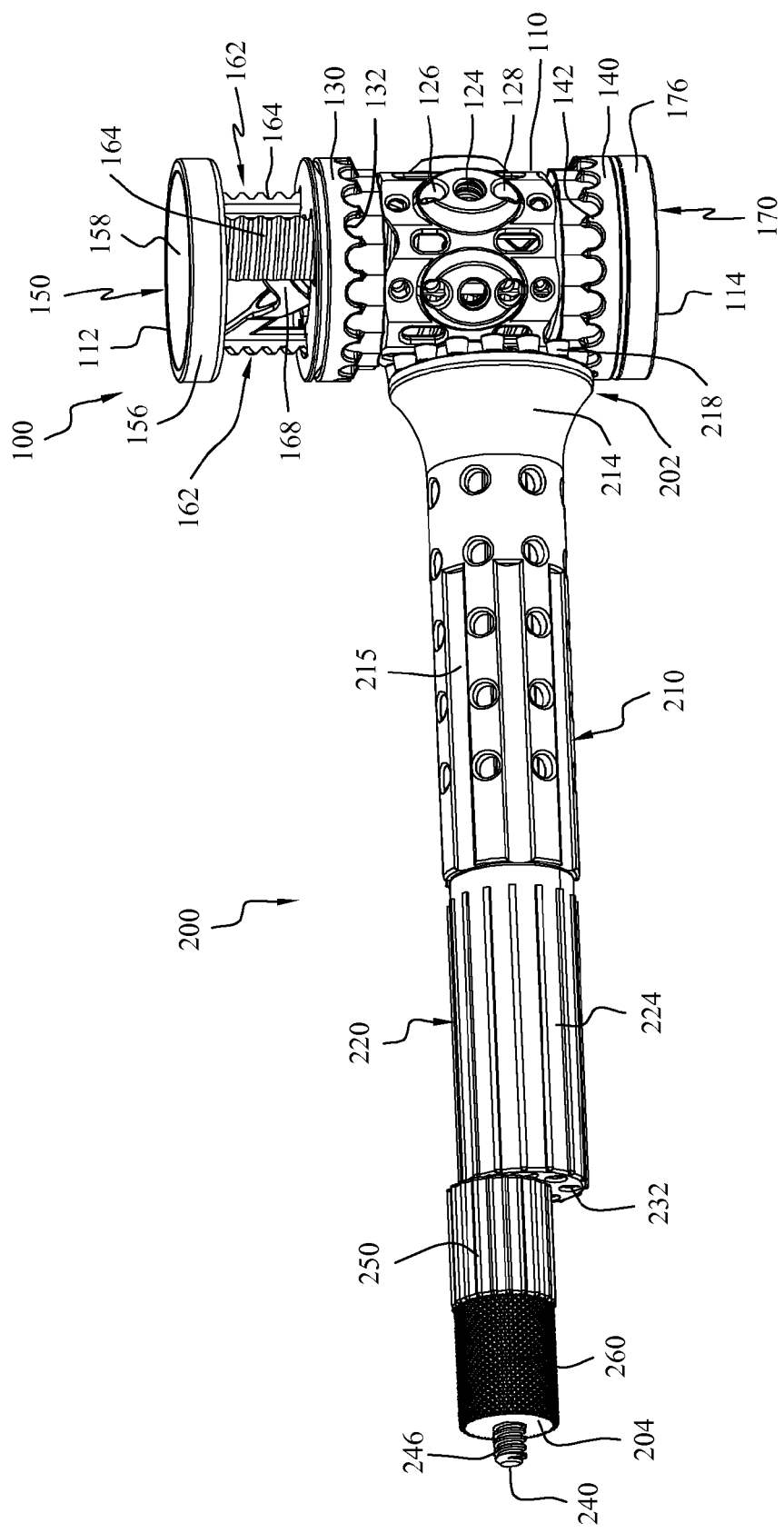
FIG. 31 is a perspective side view of the system of FIG. 24 with the tool engaging the vertebral body device in a second position, in accordance with an aspect of the present invention.
Figure 32:
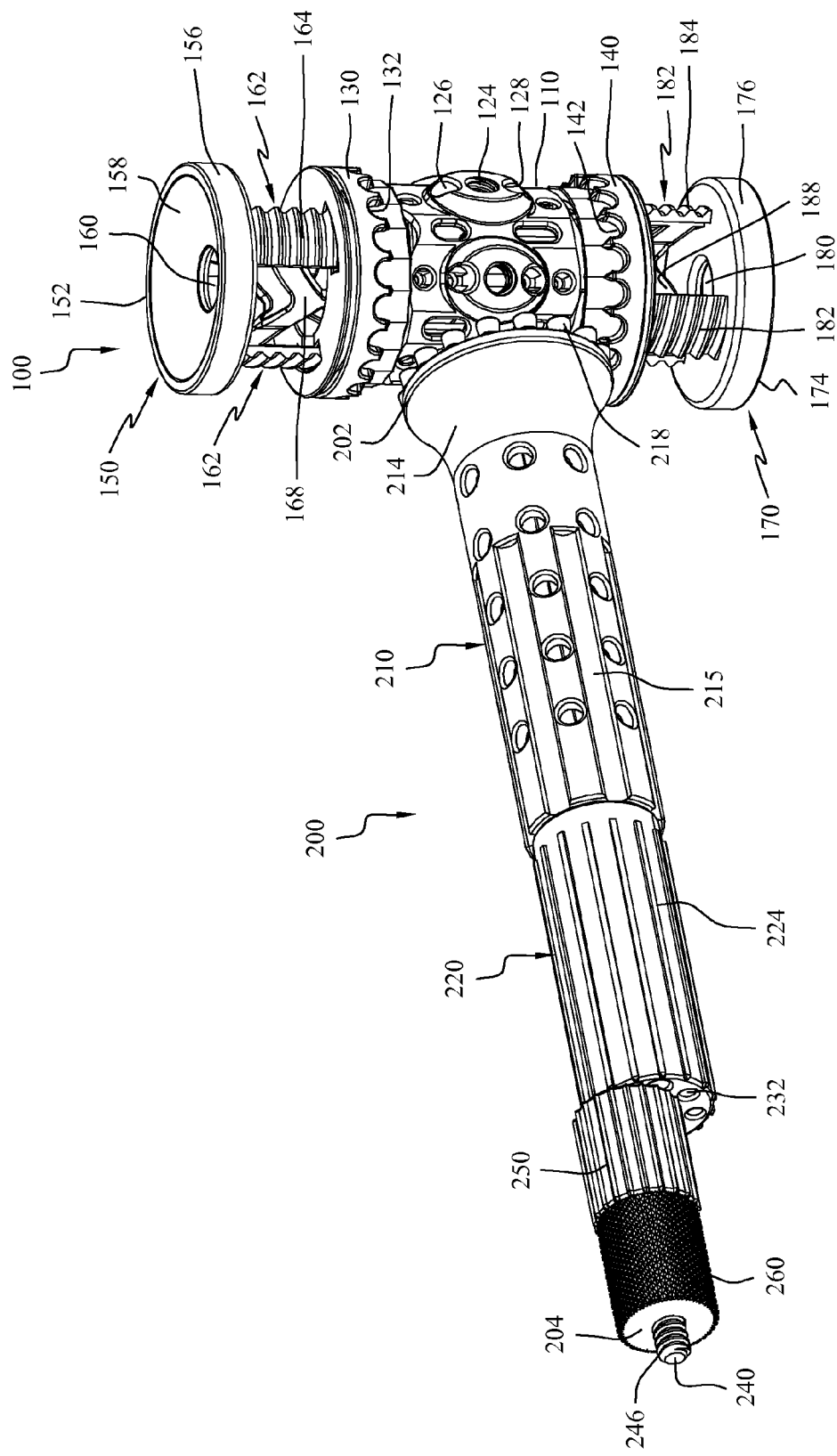
FIG. 32 is a perspective side view of the system of FIG. 24 with the second extension member in a deployed position, in accordance with an aspect of the present invention.
Figure 33:
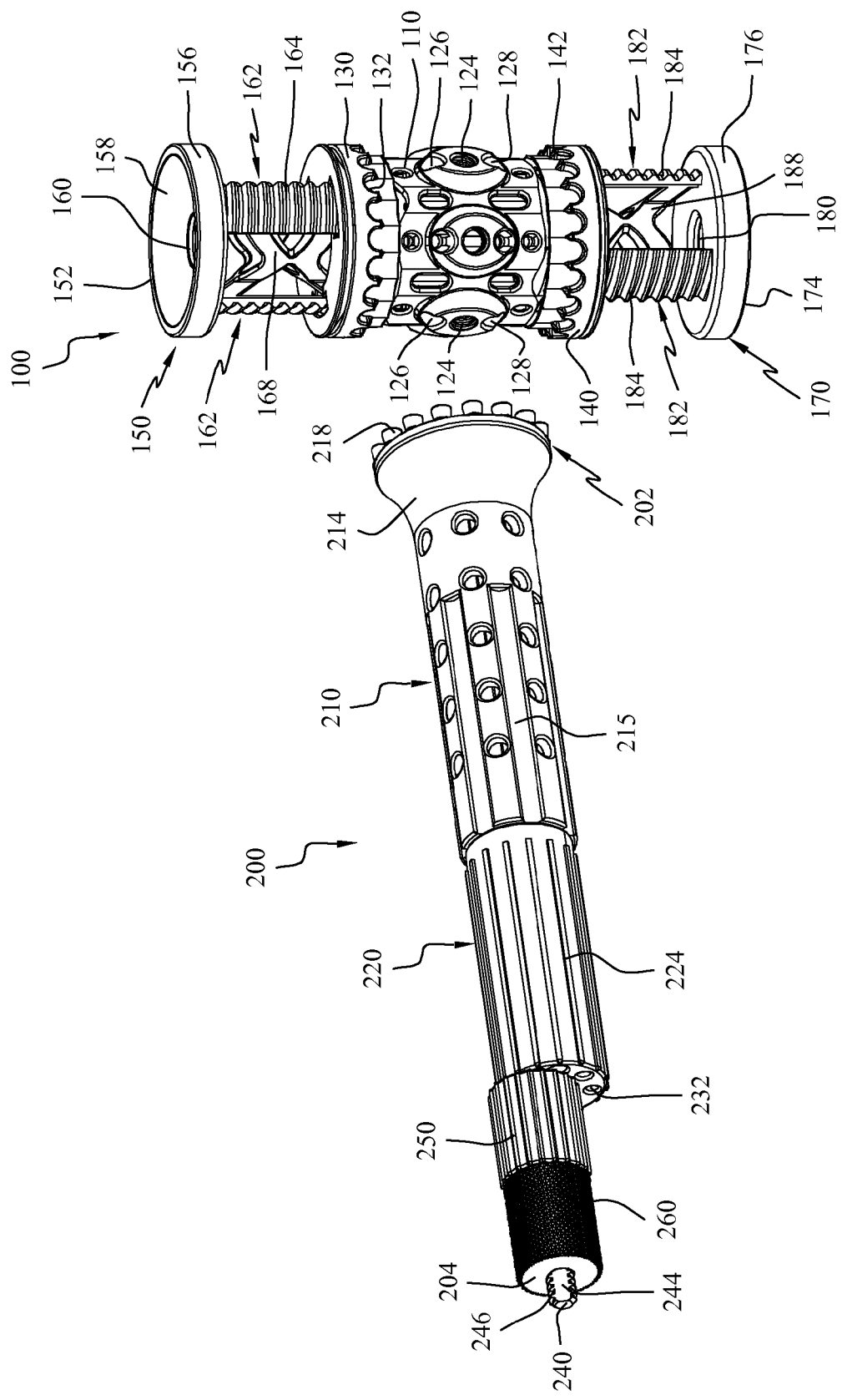
FIG. 33 is a perspective side view of the system of FIG. 24 with the tool removed from the expanded vertebral body device, in accordance with an aspect of the present invention.

Next, the adjustment member 260 may be rotated to again translate the deployment handle 210, the position selector member 220, the attachment member 250, and the adjustment member 260 toward the threaded section 242 of the rod 240. The adjustment member 260 may be rotated until the pin 228 engages a second positioning hole 128 and the projections 218 engage the grooves 142 in the second rotating member 140, as shown in FIG. 31. The handle 210 may then be rotated to engage the projections 218 in the grooves 132 causing the second rotating member 140 to turn. As the second rotating member 140 spins, the second extension member 170 may translate in a superior-inferior direction. As shown in FIG. 32, if the handle 210 is rotated in a clockwise direction, the rotating member 140 will spin in a clockwise direction, and the second extension member 170 will translate in an inferior direction increasing the height of the vertebral body device 100. Alternatively, if the handle 210 is rotated in a counterclockwise direction, the rotating member 140 will spin in a counterclockwise direction, and the second extension member 170 will translate in a superior direction decreasing the height of the vertebral body device 100. The amount of superior-inferior translation is limited by the length of the leg members 182. Once the desired configuration and height of the vertebral body device 100 is achieved, the attachment member 250 may be rotated to disengage the thread section 242 from the opening 124. After the rod 240 is removed from the vertebral body device 100, the instrument 200 may be removed from the implant 100, as shown in FIG. 33.

Figure 34:
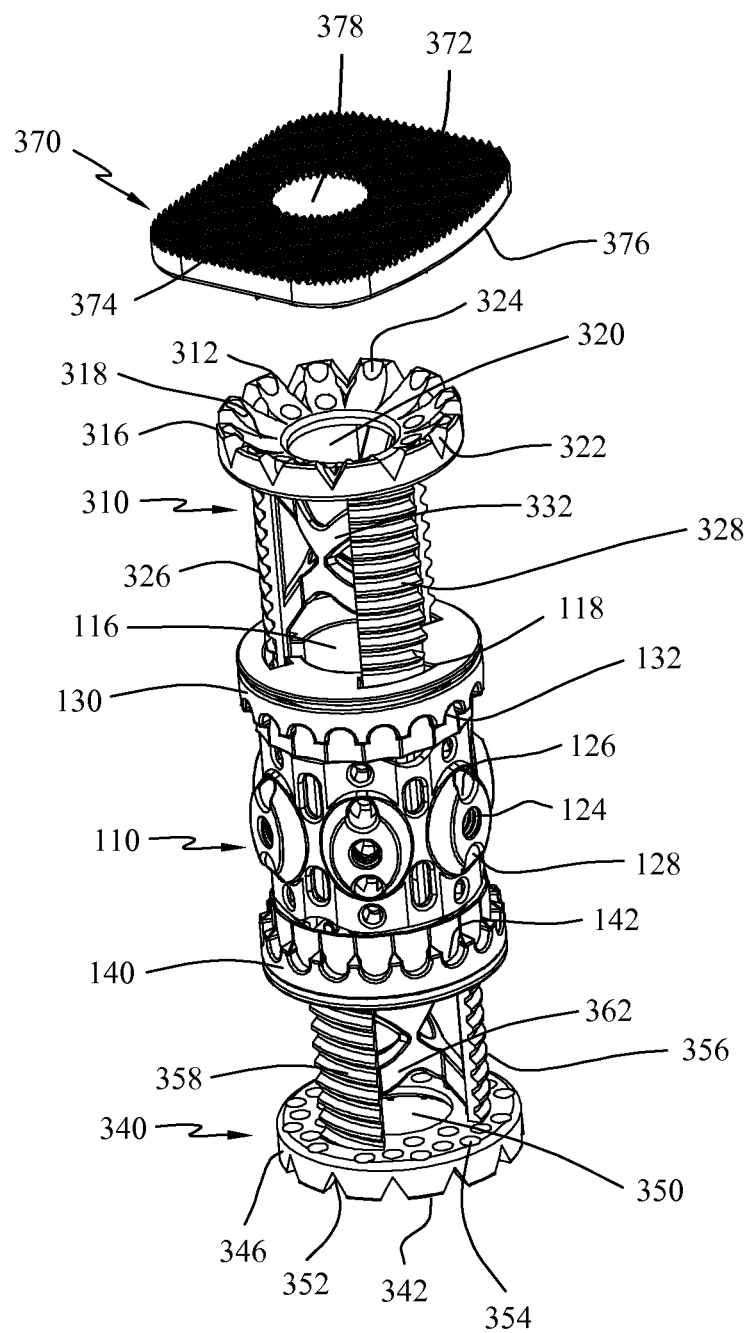
FIG. 34 is a partially exploded, perspective top view of another vertebral body device, in accordance with an aspect of the present invention.
Figure 35:
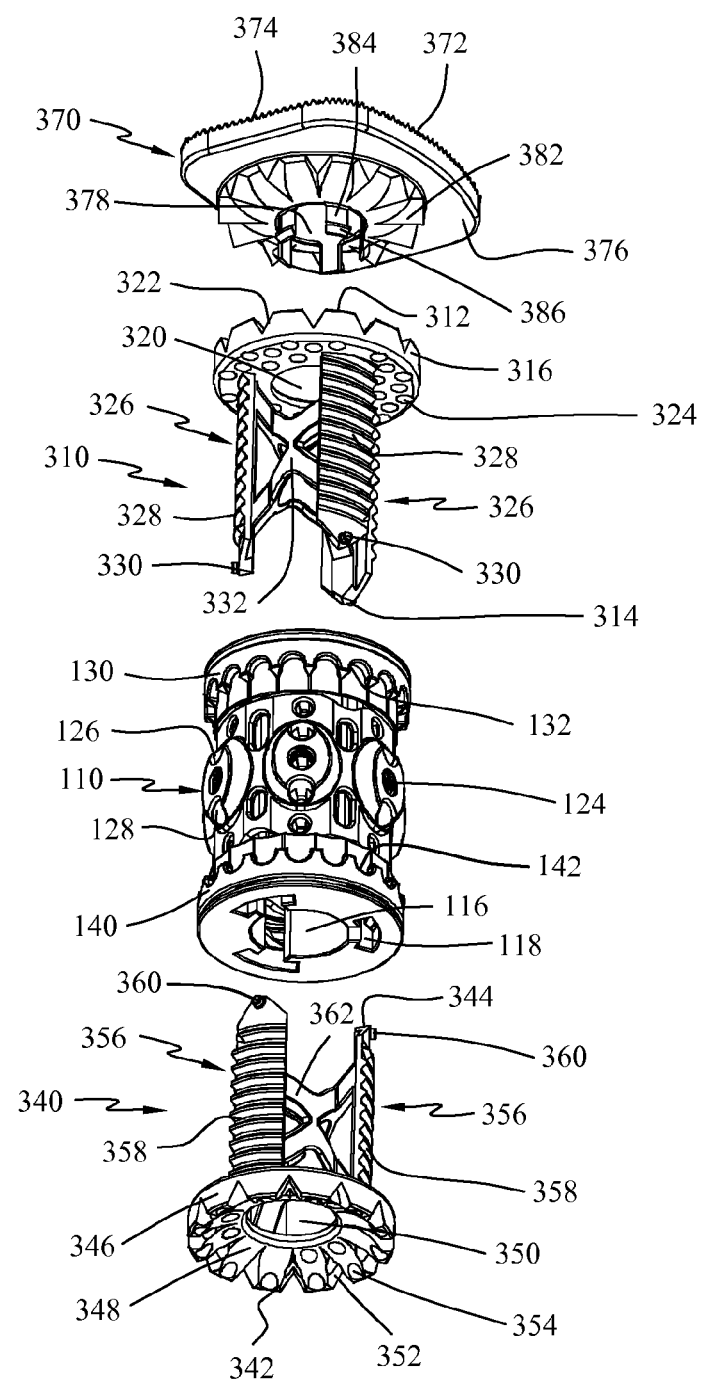
FIG. 35 is a partially exploded, perspective bottom view of the vertebral body device of FIG. 34, in accordance with an aspect of the present invention.
Figure 36:
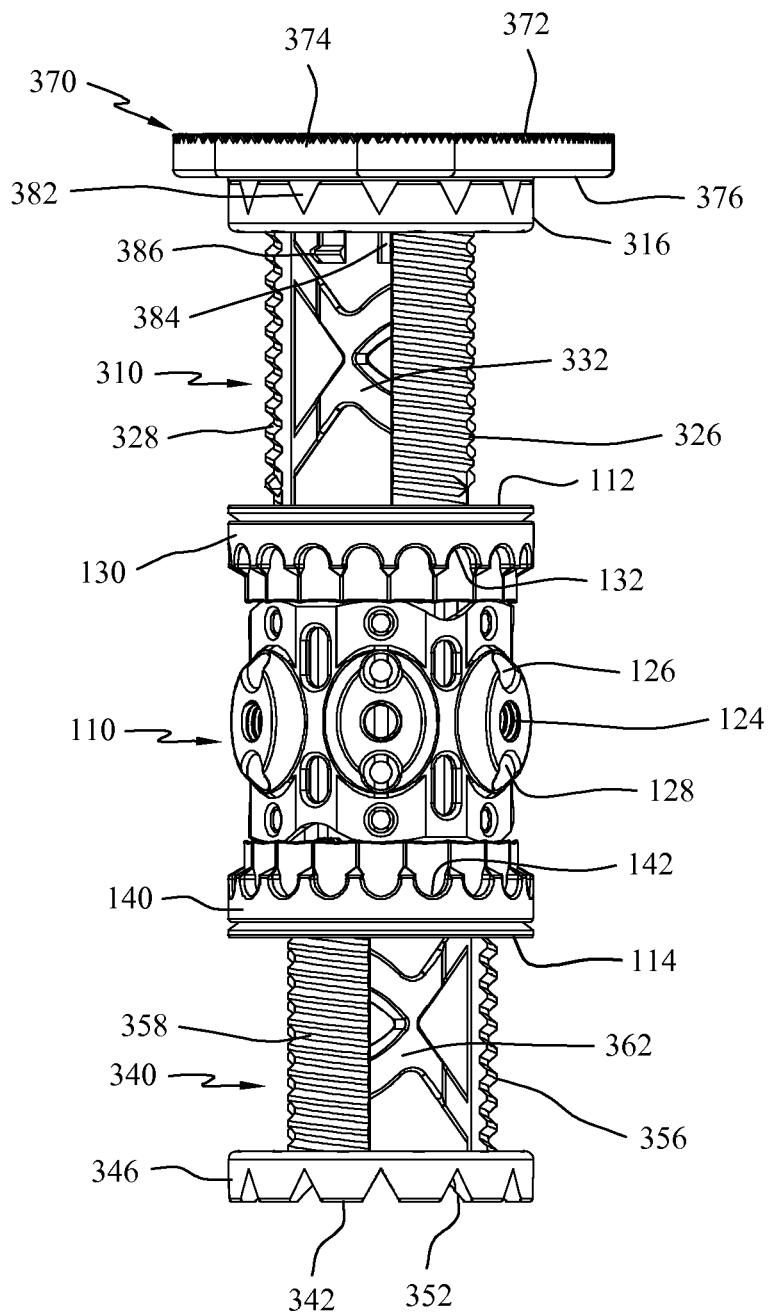
FIG. 36 is an assembled, side view of the vertebral body device of FIG. 34, in accordance with an aspect of the present invention.
Figure 37:
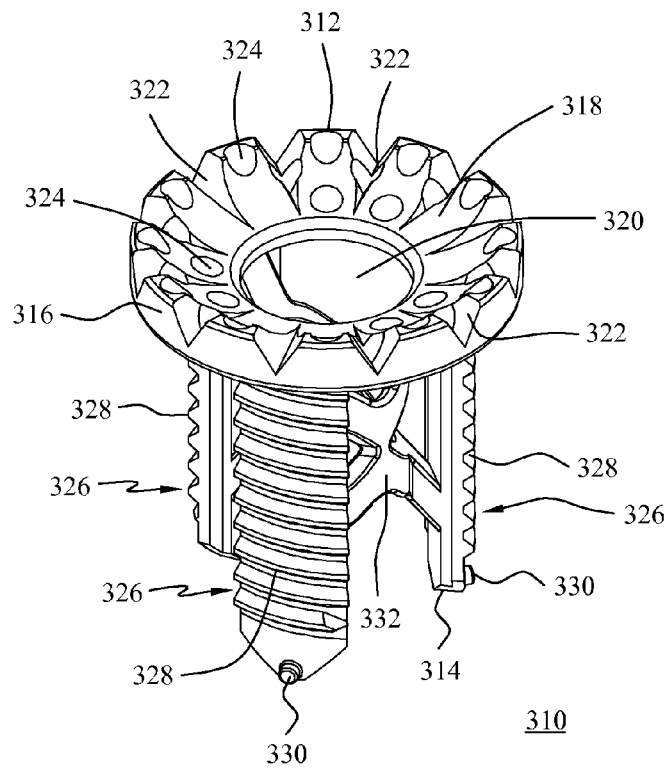
FIG. 37 is a perspective top view of a first extension member of the vertebral body device of FIG. 34, in accordance with an aspect of the present invention.
Figure 38:
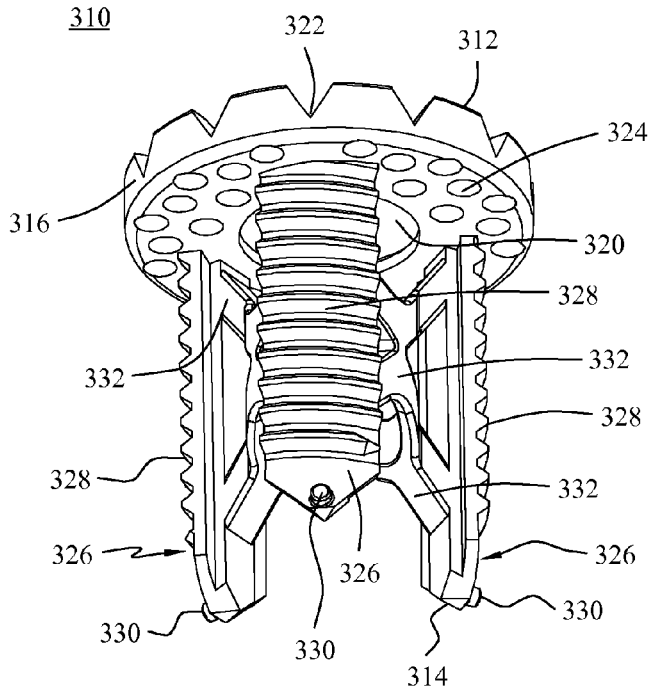
FIG. 38 is a perspective bottom view of the first extension member of FIG. 37, in accordance with an aspect of the present invention.

Another expandable vertebral body replacement device 300 is shown in FIGS. 34-36. The device 300 includes a body 110, a first rotating member 130, a second rotating member 140, a first extension member 310, a second extension member 340, and an end cap 370. The body 110, first rotating member 130, and second rotating member 140 are as described above with reference to FIGS. 1-13, which will not be described again here for brevity sake. The first extension member 310 is shown in FIGS. 35, 37, and 38. The first extension member 310 includes a first end 312 and a second end 314. The first extension member 310 may also include a top portion 316 at the first end 312 and at least one leg member 326 extending away from the top portion 316 and to the second end 314. The top portion 316 may include a curved top surface 318, for example, a hemispherical or cylindrical shaped cup. The top portion 316 may also include a center opening 320, a plurality of grooves 322, and a plurality of openings 324. The plurality of grooves 322 may be, for example, inset into the top surface 318 and surrounding the center opening 320. The plurality of openings 324 may, for example, extend through the top portion 316 from the top surface 318 entirely through the top portion 316 and may surround the center opening 320. The top surface 318 and center opening 320 may be, for example, configured to receive an end cap 370 with lordosis or a larger footprint to contact larger adjacent vertebral bodies at the outer ring of their end plates. The center opening 320 may also be configured to receive autologous bone graft or allograft material which will contact and allow for fusion with the adjacent vertebral bodies and additional graft material positioned between the at least one leg member 326.

The at least one leg member 326 may be, for example, three leg members 326, as shown in FIGS. 35, 37, and 38. The leg members 326 may include threads 328 on an exterior surface, a tab 330 on each leg member 326 positioned at the second end 314 of the first extension member 310, and support members 332 positioned between and connected to the leg members 326. The leg members 326 may be of the type described above with respect to leg members 162, 182, which will not be described again here for brevity sake.

The second extension member 340 is similar to the first extension member 310 of FIGS. 37 and 38. As shown in FIG. 35, the second extension member 340 may include a first end 342 and a second end 344. The second extension member 340 may also include a bottom portion 346 at the first end 342 and at least one leg member 356 extending away from the bottom portion 346 and to the second end 344. The bottom portion 346 may include a curved bottom surface 348, for example, a hemispherical or cylindrical shaped cup. The bottom portion 346 may also include a center opening 350, a plurality of grooves 352, and a plurality of openings 354. The plurality of grooves 352 may be, for example, inset into the bottom surface 348 and surrounding the center opening 350. The plurality of openings 354 may, for example, extend through the bottom portion 346 from the bottom surface 348 entirely through the bottom portion 346 and may surround the center opening 350. The bottom surface 348 and center opening 350 may be, for example, configured to receive an end cap 370 with lordosis or a larger footprint to contact larger adjacent vertebral bodies at the outer ring of their end plates. The center opening 350 may also be configured to receive autologous bone graft or allograft material which will contact and allow for fusion with the adjacent vertebral bodies and additional graft material positioned between the at least one leg member 356.

The at least one leg member 356 may be, for example, three leg members 356. The leg members 356 may include threads 358 on an exterior surface, a tab 360 on each leg member 356 positioned at the second end 344 of the second extension member 340, and support members 362 positioned between and connected to the leg members 356. The leg members 356 may be of the type described above with respect to leg members 162, 182, which will not be described again here for brevity sake.

Figure 39:
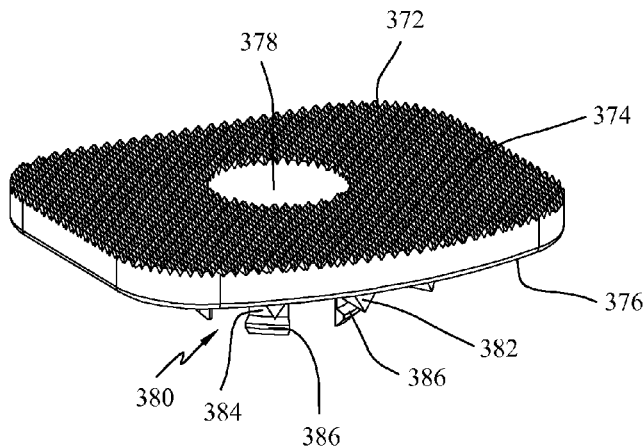
FIG. 39 is a perspective top view of an end cap of the vertebral body device of FIG. 34, in accordance with an aspect of the present invention.
Figure 40:
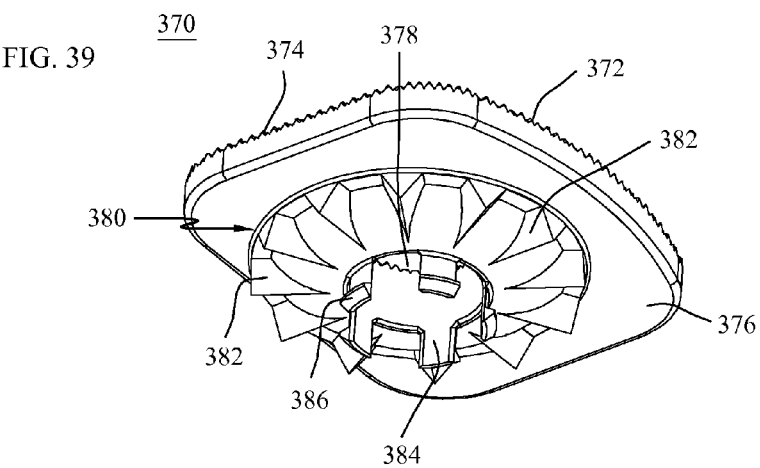
FIG. 40 is a perspective bottom view of the end cap of FIG. 39, in accordance with an aspect of the present invention.
Figure 41:
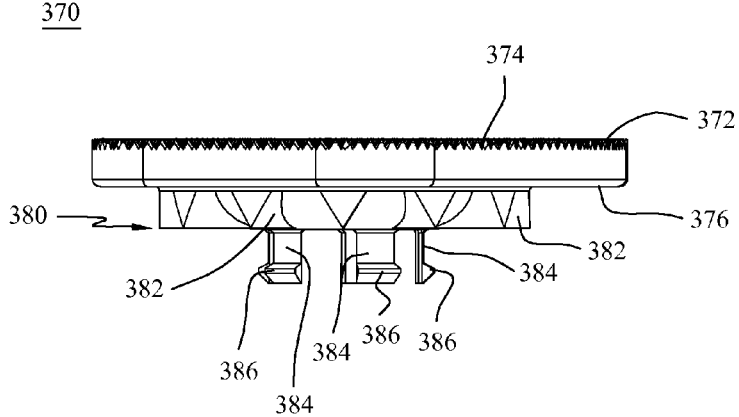
FIG. 41 is a side view of the end cap of FIG. 39, in accordance with an aspect of the present invention.
Figure 42:
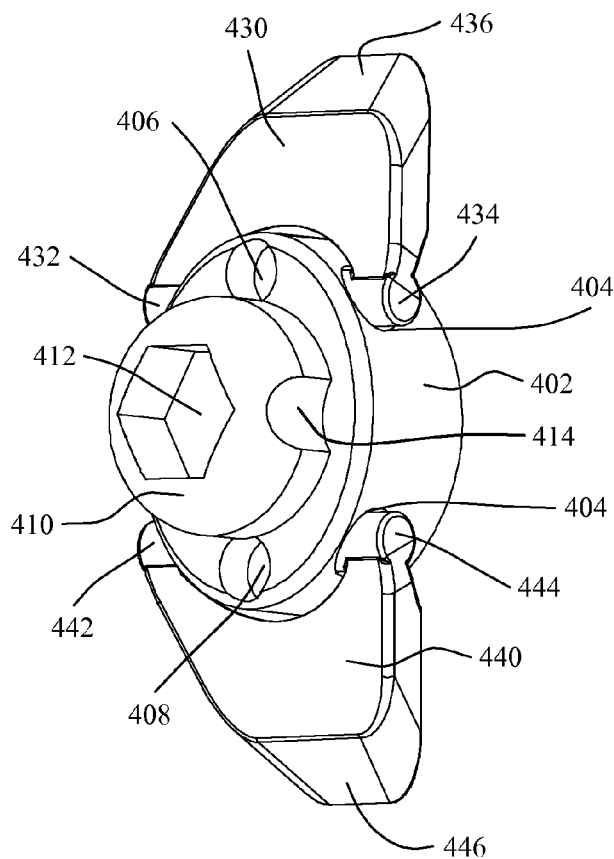
FIG. 42 is a perspective side view of a first locking member, in accordance with an aspect of the present invention.
Figure 43:
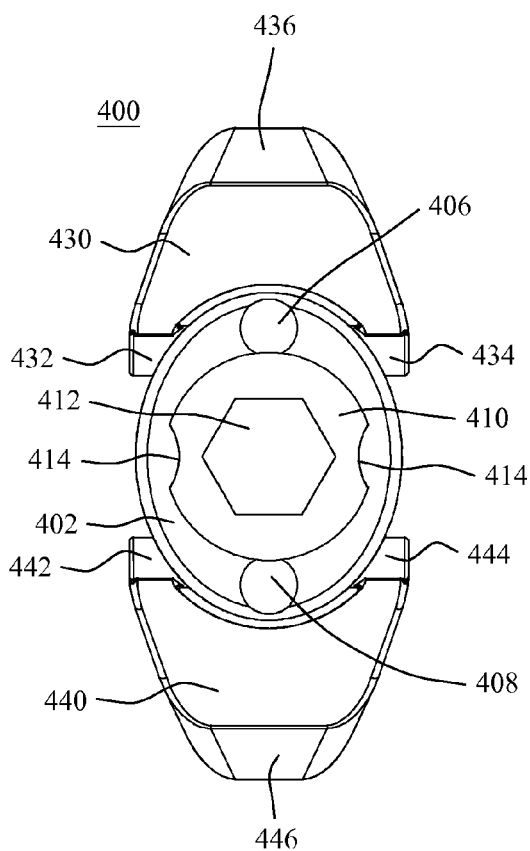
FIG. 43 is a front view of the first locking member of FIG. 42, in accordance with an aspect of the present invention.
Figure 44:
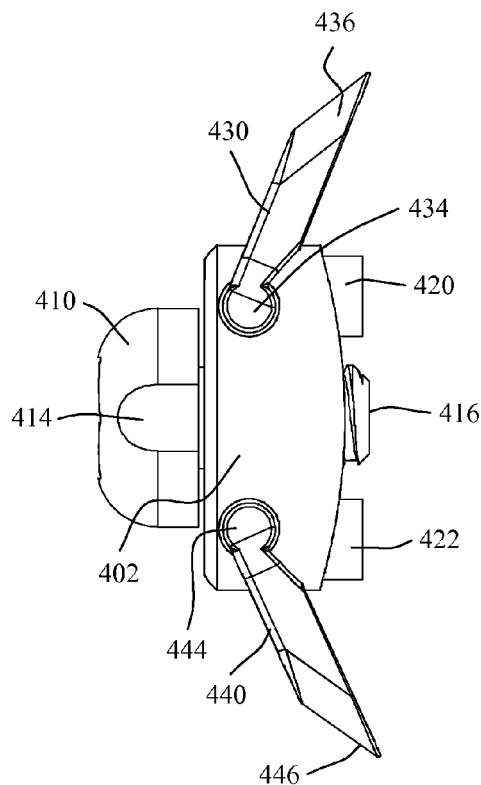
FIG. 44 is a side view of the first locking member of FIG. 42, in accordance with an aspect of the present invention.
Figure 45:
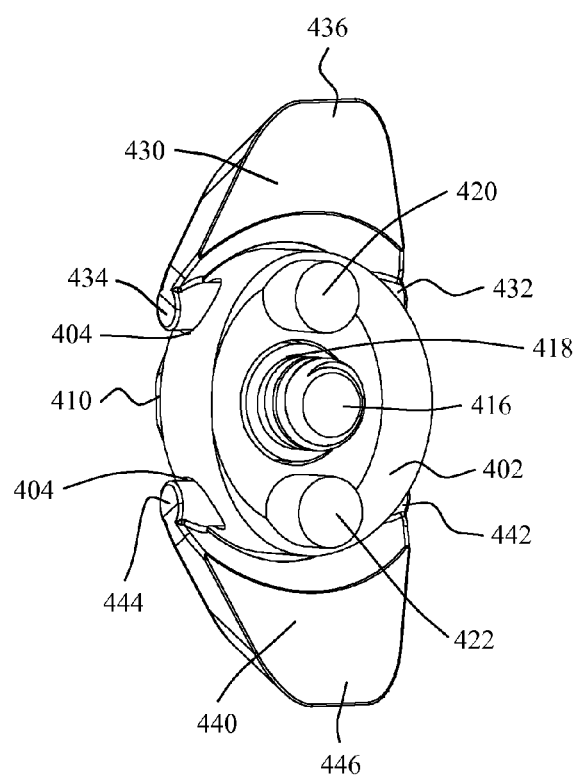
FIG. 45 is a perspective back view of the first locking member of FIG. 42, in accordance with an aspect of the present invention.
Figure 46:
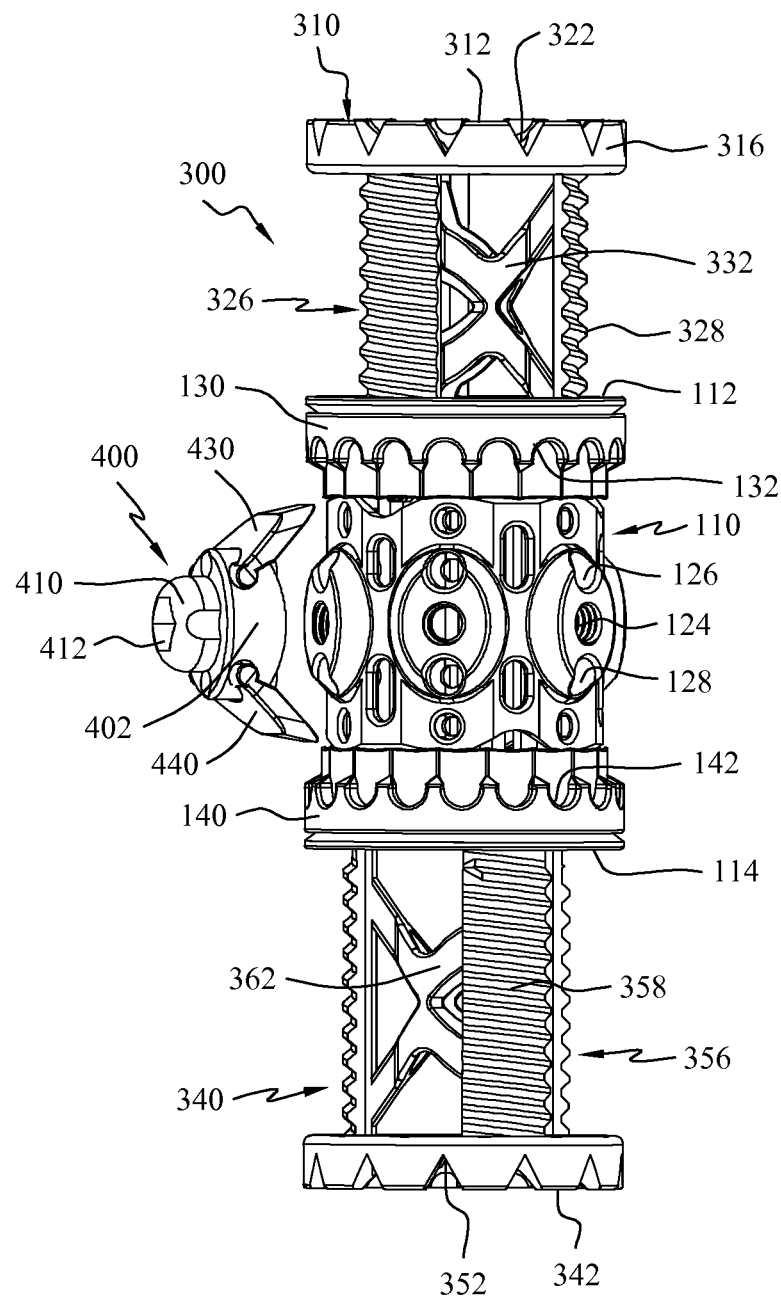
FIG. 46 is a partially exploded, perspective side view of a vertebral body device and the locking member of FIG. 42, in accordance with an aspect of the present invention.

As shown in FIGS. 39-41, the end cap 370 may include a top surface 372, a bottom surface 376, and an opening 378 extending through the end cap 370 from the top surface 372 to the bottom surface 376. The top surface 372 may have a textured surface 374, for example, grooves, teeth, ridges, or another coated, textured, or porous surface. The end cap 370 may also include an engagement portion 380 extending away from the bottom surface 376 and configured to engage at least one of the first and second extension members 310, 340. The engagement portion 380 may include teeth 382 positioned around the opening 378 and sized to fit into the grooves 322, 352 of the first and second extension members 310, 340. The engagement portion 380 may also include at least one engagement member 384 extending away from the bottom surface 376. The at least one engagement member 384 may be coupled to the bottom edge of the opening 378 at a first end. The at least one engagement member 384 may be, for example, five engagement members 384 as shown in FIGS. 35 and 40. Although alternative numbers of engagement members 384 are also contemplated. The engagement members 384 may be positioned, for example, circumferentially around the opening 378 and be sized to fit into the openings 320, 350 of the first and second extension members 310, 340. Each engagement member 384 may include a projection 386 at the second end extending away from the opening 378. The projections 386 may be sized and shaped to engage the top portion 316 of the first extension member 310 or the bottom portion 346 of the second extension member 340. The projections 386 may engage a bottom surface of the top portion 316 of the first extension member 310 and/or a top surface the bottom portion 346 of the second extension member 340 to secure the end cap 370 to at least one of the first extension member 310 and second extension member 340. Although the end cap 370 is shown with a relatively rectangular shape, the end cap 370 may have any shape desired to correspond to the shape of the vertebral body being contacted by the end cap 370.

The vertebral body replacement device 300 may be assembled as described in greater detail above with respect to vertebral body replacement device 100 and which will not be described again here for brevity sake. Assembly of the device 300 may also include inserting the engagement members 384 of the end cap 370 into the opening 320, 350 of at least one of the first and second extension members 310, 340. The method of using the device 300 may be the same or similar to the method of using the device 100 and may include use of the insertion instrument 200, as described in greater detail above and which will not be described again here for brevity sake.

The expandable vertebral body replacement devices 100, 300 may also include a locking member, for example, locking member 400 shown in FIGS. 42-49 or locking member 450 shown in FIGS. 50-56. As shown in FIGS. 42-45, the locking member 400 may include a base 402 with at least one opening 404 positioned on a side of the base and a first recess 406 and a second recess 408 positioned on the front of the base 402. The at least one opening 404 may be, for example, four openings 404 with two openings 404 positioned on opposite sides, near a top of the base 402 and two openings 404 positioned on opposite sides, near a bottom of the base 402. The base 402 may also include a hole 418 for receiving a coupling member 410. The first recess 406 may be positioned above the hole 418 and the second recess 408 may be positioned below the hole 418. The recesses 406, 408 may be sized to engage an instrument for inserting the locking member 400 into the patient to engage an expandable vertebral body replacement device 100, 300. The coupling member 410 may include a tool opening 412 positioned on the front, at least one cutout 414 on the side, and an engagement member 416 extending away from a back side. The engagement member 416 may be, for example, threaded to couple to the threads in the insertion tool opening 124 of the body 110 of the devices 100, 300. The tool opening 412 may be sized to receive a tool to rotate the coupling member 410 to insert the engagement member 416 into the opening 124 to secure the locking member 400 to the body 110. The base 402 may also include a first alignment projection 420 extending away from a back side of the base 402 and a second alignment projection 422 extending away from the back side of the base 402. The first alignment projection 420 may be positioned above the hole 418 and the second alignment projection 422 may be positioned below the hole 418. The first alignment projection 420 may be positioned to engage a first positioning hole 126 and the second alignment projection 422 may be positioned to engage a second positioning hole 128 or vice versa.

Figure 47:
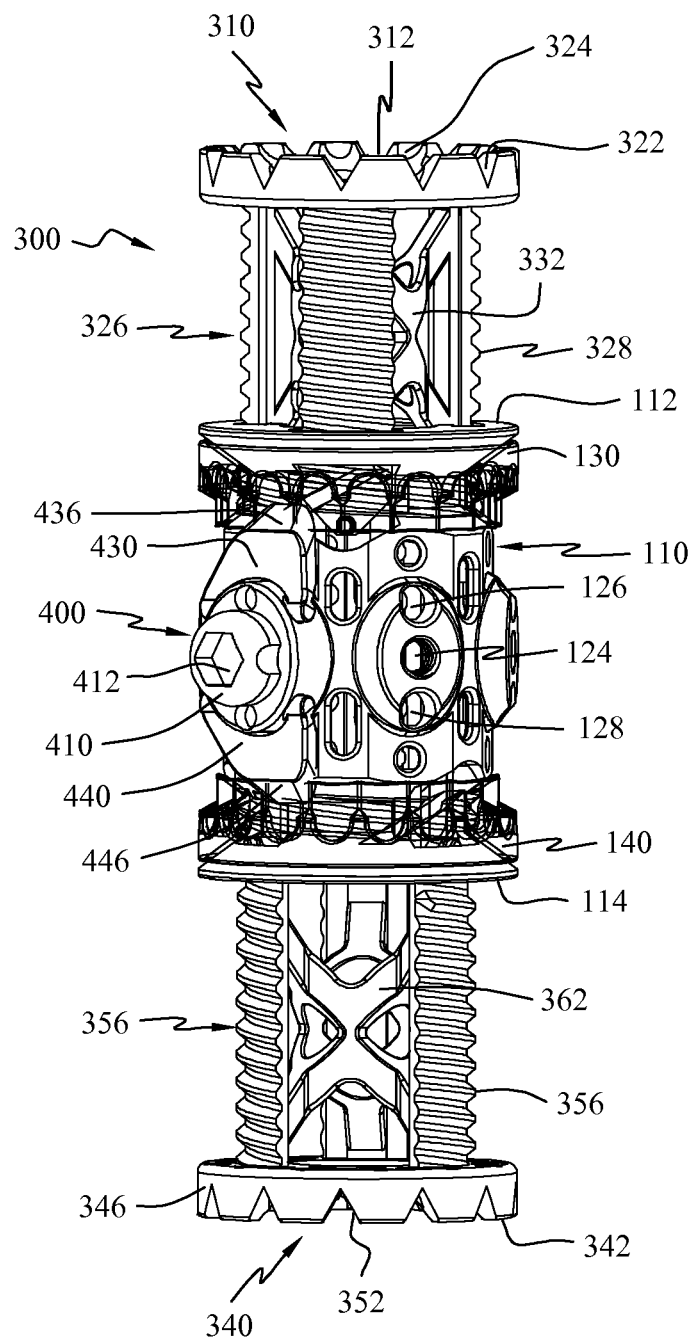
FIG. 47 is an assembled, perspective side view of the vertebral body device and locking member of FIG. 46 with transparent rotating members, in accordance with an aspect of the present invention.
Figure 48:
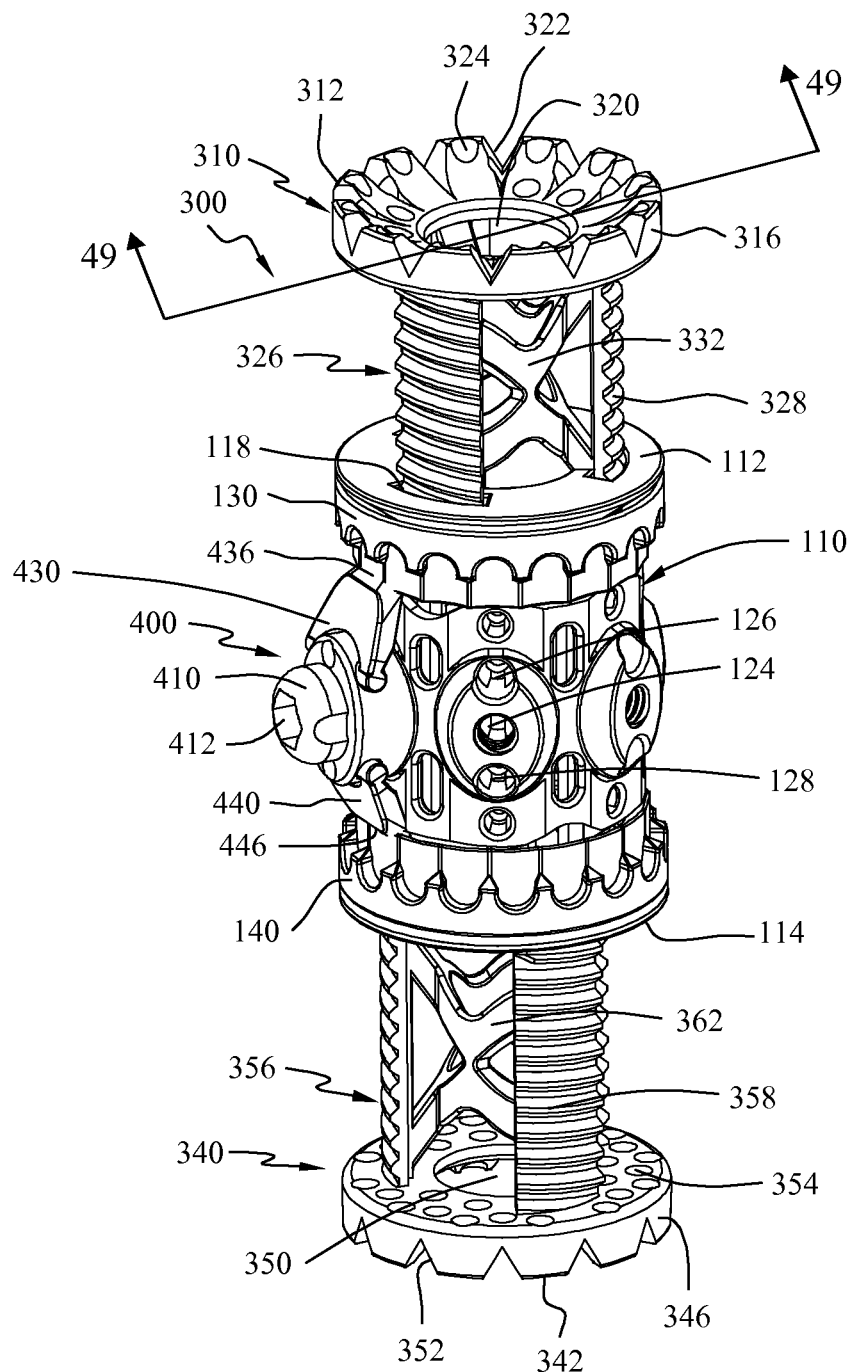
FIG. 48 is an assembled, perspective top view of the vertebral body device and locking member of FIG. 46, in accordance with an aspect of the present invention.
Figure 49:
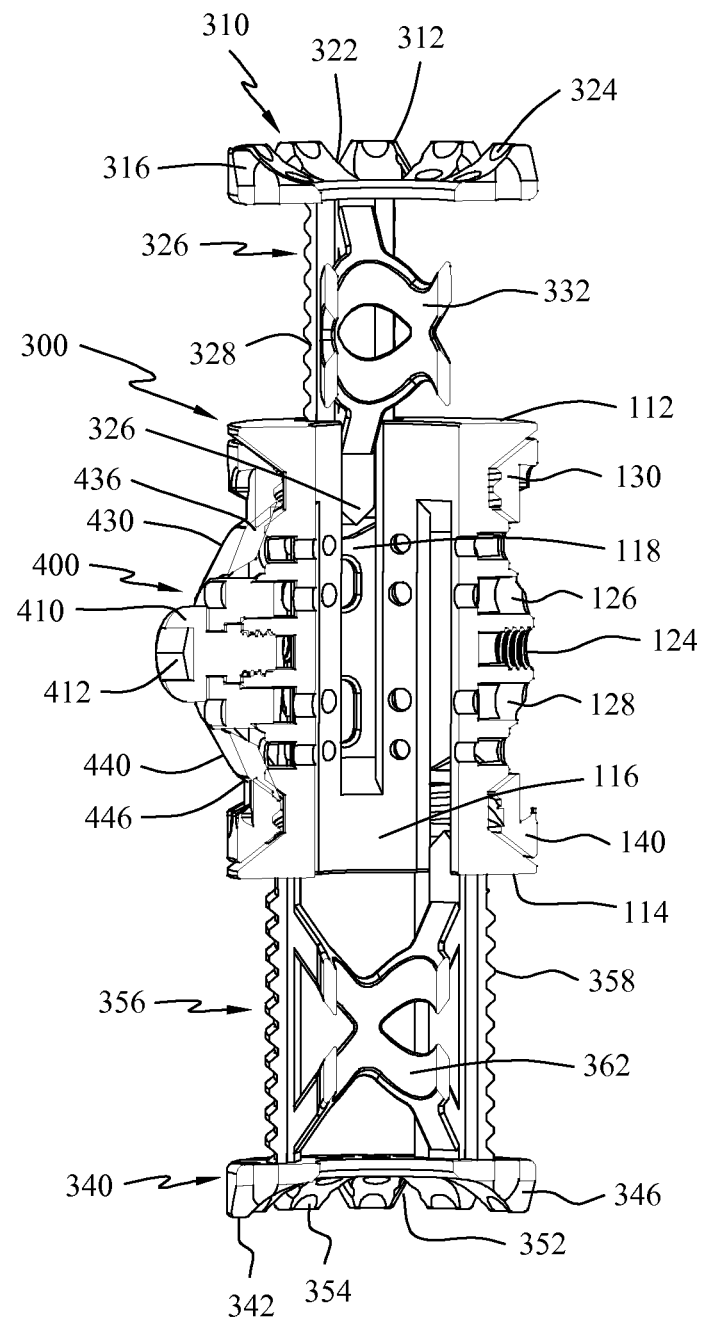
FIG. 49 is a cross-sectional view of the vertebral body device and locking member of FIG. 46 taken along line 49-49 in FIG. 48, in accordance with an aspect of the present invention.
Figure 50:
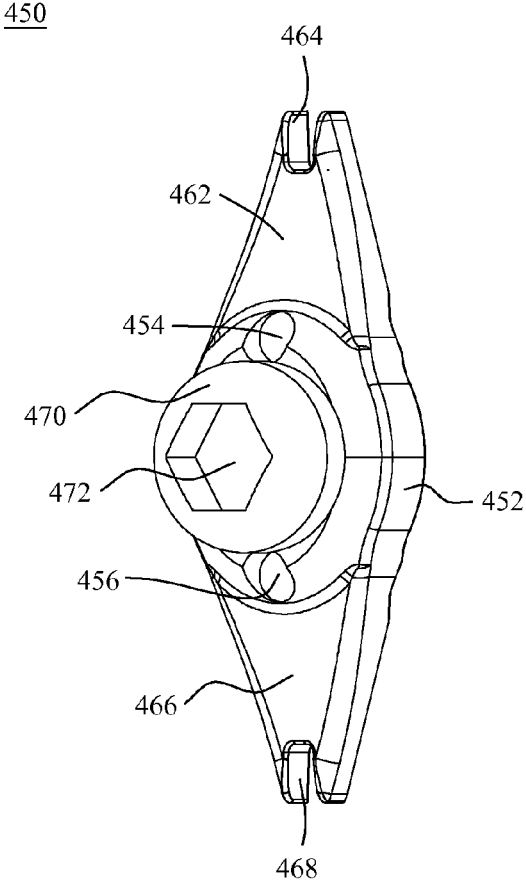
FIG. 50 is a perspective front view of a second locking member, in accordance with an aspect of the present invention.
Figure 51:
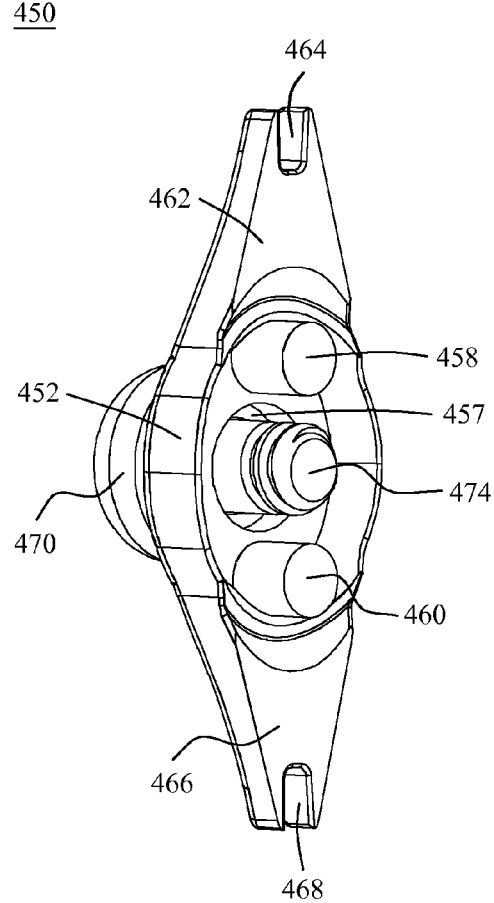
FIG. 51 is a perspective back view of the second locking member of FIG. 50, in accordance with an aspect of the present invention.
Figure 52:
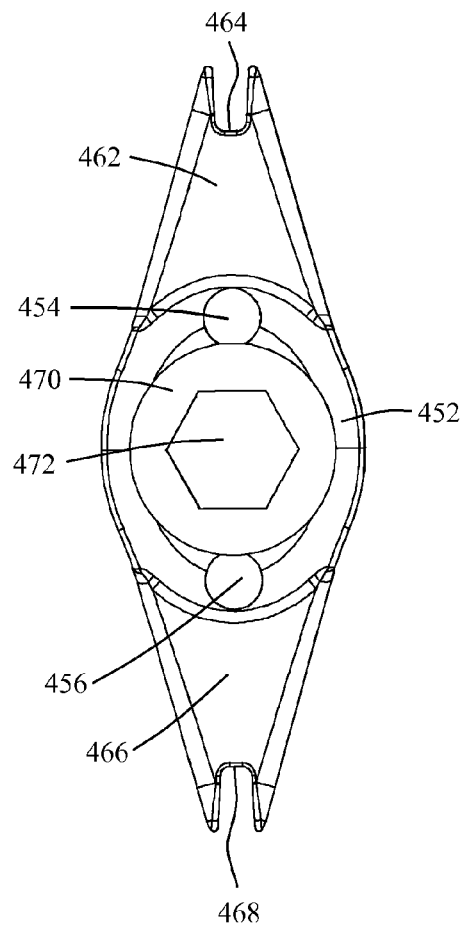
FIG. 52 is a front view of the second locking member of FIG. 50, in accordance with an aspect of the present invention.
Figure 53:
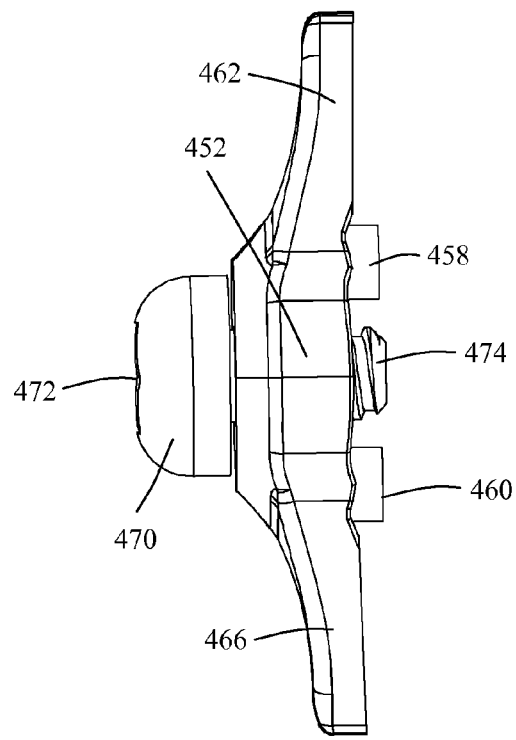
FIG. 53 is a side view of the second locking member of FIG. 50, in accordance with an aspect of the present invention.

The locking member 400 may also include a first wing member 430 rotatably coupled to a top of the base 402 and a second wing member 440 rotatably coupled to a bottom of the base 402. The first wing member 430 may include a first hinge 432 and a second hinge 434 on a first end of the first wing member 430. The first hinge 432 may be positioned on a first side of the wing member 430 and the second hinge 434 may be positioned on a second side of the wing member 430 opposite the first side. The first and second hinges 432, 434 may engage openings 404 positioned near the top of the base 402. The first wing member 430 may also include, for example, a tapered end 436 positioned on a second end of the first wing member 430 opposite the first end. The tapered end 436 may be sized to extend between the body 110 and one of the first rotating member 130 and second rotating member 140, as shown in FIGS. 47-49. The second wing member 440 may include a first hinge 442 and a second hinge 444 on a first end of the second wing member 440. The first hinge 442 may be positioned on a first side of the wing member 440 and the second hinge 444 may be positioned on a second side of the wing member 440 opposite the first side.

The first and second hinges 442, 444 may engage openings 404 positioned near the bottom of the base 402. The second wing member 440 may also include, for example, a tapered end 446 positioned on a second end of the second wing member 440 opposite the first end. The tapered end 446 may be sized to extend between the body 110 and one of the first rotating member 130 and second rotating member 140, as shown in FIGS. 47-49.

With continued reference to FIGS. 47-49, once the device 300 is in the desired position, a locking member 400 may be inserted to secure the device 300 in the desired position. The locking member 400 may be inserted by coupling the locking member 400 to an insertion tool (not shown) with the wing members 430, 440 in an angled position. The first alignment projection 420 may be, for example, aligned with alignment opening 126 and the second alignment projection 422 may be, for example, aligned with alignment opening 128. The projections 420, 422 of the locking member 400 may then be inserted into the openings 126, 128 of the body 110, as shown in FIG. 47. Then, a driver (not shown) may be inserted into the tool opening 412 and the coupling member 410 may be rotated to secure the locking member 400 to the body 110. As the coupling member 410 is rotated the wing members 430, 440 engage the side of the body 110, the first wing member 430 may, for example, slide between the body 110 and the first rotating member 130 and the second wing member 440 may slide between the body 110 and the second rotating member 140. The tapered ends 436, 446 of the wing members 430, 440 may, for example, act as wedges to secure the rotating members 130, 140 and prevent them from rotating in order to secure the extension members 310, 340 in the desired position.

As shown in FIGS. 50-56, the locking member 450 may include a body 452 with a first recess 454, a second recess 456, and a hole 457. The first and second recess 454, 456 may be positioned on the front of the body 452. The hole 457 may be sized to receive a coupling member 470. The first recess 454 may be positioned above the hole 457 and the second recess 456 may be positioned below the hole 457. The recesses 454, 456 may be sized to engage an instrument for inserting the locking member 450 into the patient to engage an expandable vertebral body replacement device 100, 300. The body 452 may also include a first alignment projection 458 extending away from a back side of the body 452 and a second alignment projection 460 extending away from the back side of the body 452. The first alignment projection 458 may be positioned above the hole 457 and the second alignment projection 460 may be positioned below the hole 457. The first alignment projection 458 may be positioned to engage a first positioning hole 126 and the second alignment projection 460 may be positioned to engage a second positioning hole 128 or vice versa.

The body 542 may also include a first extension member 462 extending away from a top of the body 452 and a second extension member 466 extending away from a bottom of the body 452. The first extension member 462 may include a first channel 464 for engaging at least one groove 132, 142 of a rotating member 130, 140 to secure the device 100, 300 in the desired position. The second extension member 466 may include a second channel 468 for engaging at least one groove 132, 142 of a rotating member 130, 140 to secure the device 100, 300 in the desired position. The extension members 462, 466 may have, for example, a generally triangular shape, although other shapes are also contemplated.

The coupling member 470 may include a tool opening 472 positioned on the front and an engagement member 474 extending away from a back side. The engagement member 474 may be, for example, threaded to couple to the threads in the insertion tool opening 124 of the body 110 of the devices 100, 300. The tool opening 472 may be sized to receive a tool to rotate the coupling member 470. As the coupling member 470 is rotated the engagement member 474 is inserted into the opening 124 and the locking member 450 is secured to the body 110.

Figure 54:
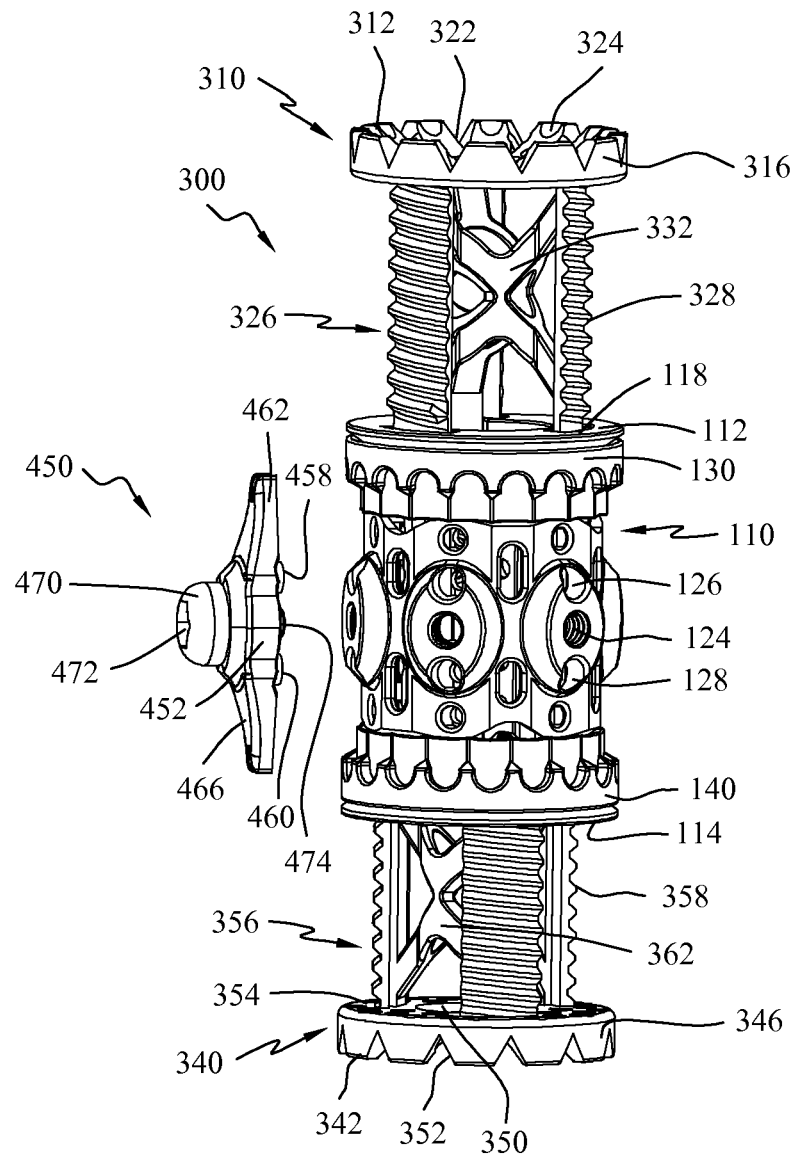
FIG. 54 is a partially exploded, perspective side view of a vertebral body device and the locking member of FIG. 50, in accordance with an aspect of the present invention.
Figure 55:
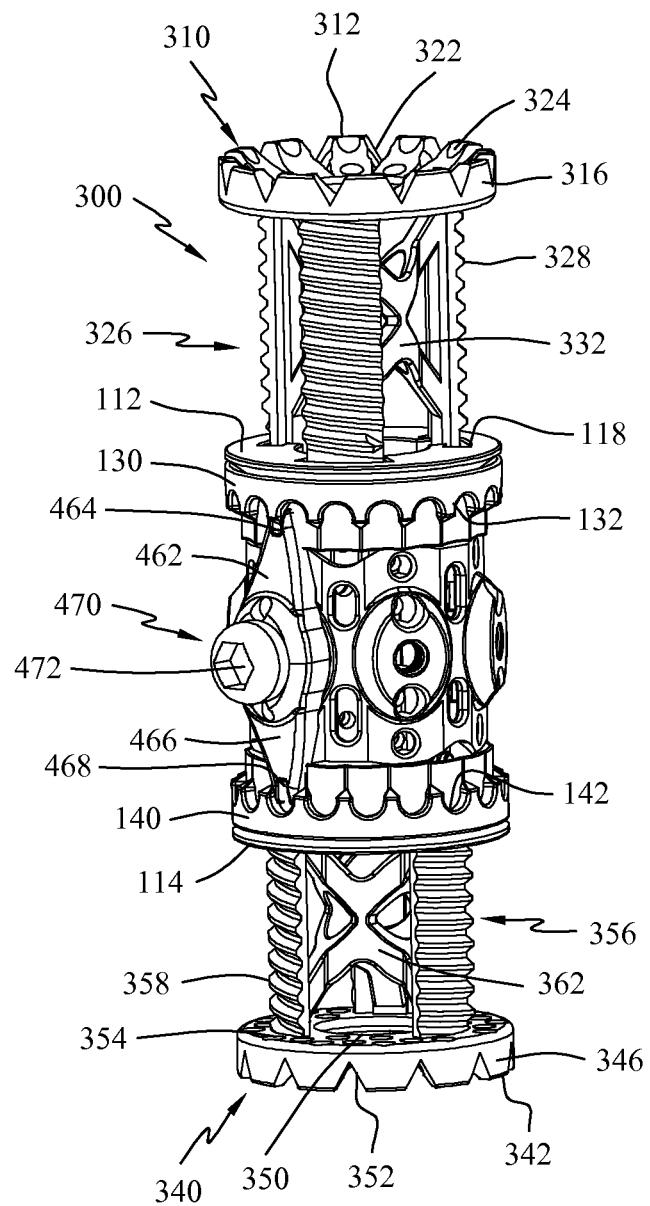
FIG. 55 is an assembled, perspective side view of the vertebral body device and locking member of FIG. 54, in accordance with an aspect of the present invention.
Figure 56:
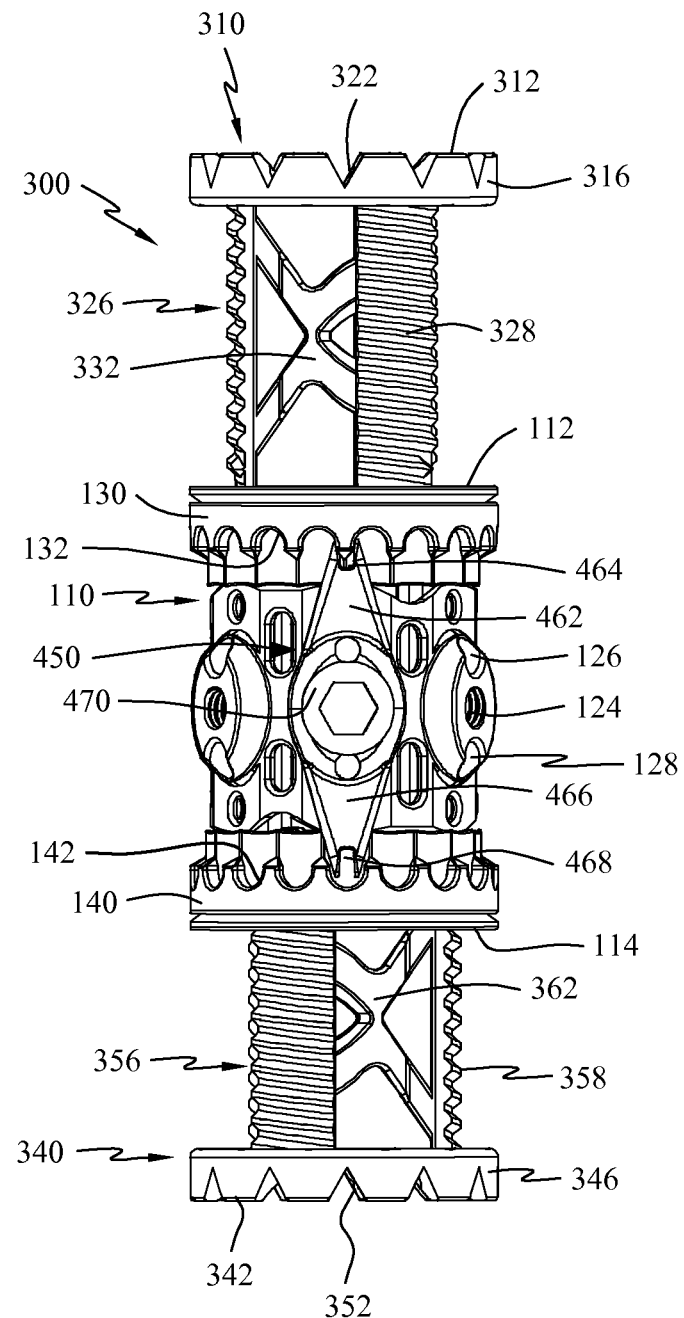
FIG. 56 is a front view of the vertebral body device and locking member of FIG. 54, in accordance with an aspect of the present invention.

As shown in FIGS. 54-56, once the device 300 is in the desired position, a locking member 450 may be inserted to secure the device 300 in the desired position. The locking member 450 may be inserted by coupling the locking member 450 to an insertion tool (not shown). The first alignment projection 458 may be, for example, aligned with alignment opening 126 and the second alignment projection 460 may be, for example, aligned with alignment opening 128. The projections 458, 460 of the locking member 450 may then be inserted into the openings 126, 128 of the body 110, as shown in FIG. 55. Next, a driver (not shown) may be inserted into the tool opening 472 and the coupling member 470 may be rotated to secure the locking member 450 to the body 110. As the coupling member 470 is rotated the channels 464, 468 engage the gears 132, 142 of the first and second rotating members 130, 140. A tooth of the gears 132, 142 may be, for example, positioned within the channels 464, 468 of the locking member 450 or the end of the locking member 450 with the channels 464, 468 may be positioned in the groove of the gears 132, 142 to secure the rotating members 130, 140 and lock the device 300 in the desired position.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. An expandable cage system, comprising:
   a vertebral body device, comprising:
   a body with a first end and a second end, the body comprising:
   a plurality of apertures positioned around the body along a midpoint between the first end and the second end, each of the plurality of apertures spaced apart from the adjacent apertures;
   a plurality of first positioning holes positioned superior to each of the plurality of apertures; and
   a plurality of second positioning holes positioned inferior to each of the plurality of apertures;
   a first rotating member coupled to the first end;
   a second rotating member coupled to the second end;
   a first extension member moveably coupled to the first end; and
   a second extension member moveably coupled to the second end; and
   an insertion instrument, wherein the plurality of apertures, the plurality of first positioning holes, and the plurality of second positioning holes are sized to receive the insertion instrument, the insertion instrument comprising:
   a deployment handle;
   a position selector member rotatably coupled to the deployment handle;
   a rod extending through an opening in the position selector member, the rod comprising:
   a threaded section configured to couple to an opening in the body of the vertebral body device;
   an implant attachment member coupled to a portion of the rod; and
   a tension adjustment member rotatably coupled to the rod at a second end.

2. The expandable cage system of claim 1, wherein the body further comprises:
   a first groove positioned near the first end for receiving the first rotating member; and
   a second groove positioned near the second end for receiving the second rotating member.

3. The expandable cage system of claim 2, wherein the first rotating member comprises:
   a center opening forming an interior surface, wherein the interior surface comprises:
   threads positioned on the interior surface; and
   at least one first angled slot positioned on the interior surface and intersecting the threads; and
   a plurality of grooves positioned around an exterior surface, wherein the plurality of grooves are undercut toward the interior surface.

4. The expandable cage system of claim 3, wherein the second rotating member comprises:
   a center opening forming an interior surface, wherein the interior surface comprises:
   threads positioned on the interior surface; and
   at least one second angled slot positioned on the interior surface and intersecting the threads; and
   a plurality of grooves positioned around the exterior surface, wherein the plurality of grooves are undercut toward the interior surface.

5. The expandable cage system of claim 4, wherein the first extension member comprises:
   a top portion;
   at least one first leg member extending away from the top portion; and
   at least one first support member positioned between and coupled to the at least one first leg member.

6. The expandable cage system of claim 5, wherein the second extension member comprises:

a bottom portion;
at least one second leg member extending away from the bottom portion; and
at least one second support member positioned between and coupled to the at least one second leg member.

7. The expandable cage system of claim 6, wherein the at least one first leg member comprises:
threads positioned on an exterior surface of the at least one first leg member and configured to engage the threads on the interior surface of the first rotating member; and
a tab positioned on a second end of the at least one first leg member and configured to engage the at least one first angled slot of the first rotating member.

8. The expandable cage system of claim 6, wherein the top portion comprises:
a center opening extending from a top surface to a bottom surface of the top portion; and
a plurality of grooves in the top surface and positioned circumferentially around the center opening; and
wherein the bottom portion comprises:
a center opening extending from a bottom surface to a top surface of the bottom portion; and
a plurality of grooves in the bottom surface and positioned circumferentially around the center opening.

9. The expandable cage system of claim 7, wherein the at least one second leg member comprises:
threads positioned on an exterior surface of the at least one second leg member and configured to engage the threads on the interior surface of the second rotating member; and
a tab positioned on a second end of the at least one second leg member and configured to engage the at least one second angled slot of the second rotating member.

10. The expandable cage system of claim 1, wherein the position selector member comprises:
a pin extending away from a first end of the position selector member and configured to engage at least one positioning hole in the body of the vertebral body device, the at least one positioning hole positioned adjacent to the opening.

11. The expandable cage system of claim 10, wherein the deployment handle comprises:
a plurality of projections configured to engage and rotate the first rotating member and the second rotating member, wherein the plurality of projections are cone shaped to engage at least one of the first rotating member and the second rotating member.

12. A method of using an expandable cage system, comprising:
obtaining a vertebral body device, the vertebral body comprising:
a body with a first end and a second end;
a first rotating member rotatably coupled to the first end;
a second rotating member rotatably coupled to the second end;
a first extension member moveably coupled to the first end; and
a second extension member moveably coupled to the second end;
obtaining an insertion instrument, the insertion instrument comprising:
a deployment handle;
a position selector member rotatably coupled to the deployment handle;
a rod extending through an opening in the position selector member;
an attachment member coupled to a portion of the rod; and
an adjustment member rotatably coupled to the rod at a second end;
coupling the vertebral body device to the insertion instrument, comprising:
aligning a first end of the rod with an opening in the body of the vertebral body device;
rotating the implant attachment member to couple the rod to the body of the vertebral body device; and
rotating the adjustment member to position the deployment handle for engagement with the first rotating member;
inserting the vertebral body device into a patient between two vertebral bodies;
expanding the vertebral body device;
removing the insertion instrument; and
closing the patient.

13. The method of claim 12, wherein expanding the vertebral body device comprises:
rotating the deployment handle in a first direction to engage and rotate the first rotating member in a second direction, wherein rotating the first rotating member translates the coupled first extension member to increase a height of the vertebral body device.

* * * * *